US010571460B2

(12) United States Patent
Sussman et al.

(10) Patent No.: US 10,571,460 B2
(45) Date of Patent: Feb. 25, 2020

(54) METHODS, SYSTEMS, AND COMPOSITIONS FOR STUDYING SOLVENT ACCESSIBILITY AND THREE-DIMENSIONAL STRUCTURE OF BIOLOGICAL MOLECULES

(71) Applicant: Wisconsin Alumni Research Foundation, Madison, WI (US)

(72) Inventors: Michael R. Sussman, Cross Plains, WI (US); J. Leon Shohet, Madison, WI (US); Faraz A. Choudhury, Madison, WI (US); Joshua M. Blatz, Monona, WI (US); Benjamin B. Minkoff, Madison, WI (US); Daniel I. Benjamin, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 30 days.

(21) Appl. No.: 15/600,352

(22) Filed: May 19, 2017

(65) Prior Publication Data

US 2017/0336390 A1 Nov. 23, 2017

Related U.S. Application Data

(60) Provisional application No. 62/338,699, filed on May 19, 2016.

(51) Int. Cl.
*H05H 1/24* (2006.01)
*G01N 33/50* (2006.01)
(Continued)

(52) U.S. Cl.
CPC ............ *G01N 33/50* (2013.01); *B01J 19/088* (2013.01); *C12Q 1/6876* (2013.01); *G01N 1/28* (2013.01); *G01N 33/487* (2013.01); *G01N 33/6848* (2013.01); *H05H 1/24* (2013.01); *B01J 2219/0809* (2013.01); *B01J 2219/0894* (2013.01); *G01N 2333/765* (2013.01); *G01N 2333/90216* (2013.01); *G01N 2333/91215* (2013.01); *G01N 2440/00* (2013.01); *H01J 49/0031* (2013.01)

(58) Field of Classification Search
None
See application file for complete search history.

(56) References Cited

U.S. PATENT DOCUMENTS 6,815,540 B1 * 11/2004 Pluckthun ............... C07K 16/00
435/320.1
2003/0208038 A1 * 11/2003 Anderson ................. C07K 1/13
530/345

(Continued)

OTHER PUBLICATIONS

Maleknia et al, Rapid Comm. Mass Spec., vol. 13, pp. 2352-2358. (Year: 1999).*

(Continued)

*Primary Examiner* — Robert T. Crow
(74) *Attorney, Agent, or Firm* — Quarles & Brady LLP

(57) ABSTRACT

This disclosure provides methods, systems, and compositions of matter for studying solvent accessibility and three-dimensional structure of biological molecules. A plasma can be used to generate marker radicals, which can interact with a biological molecule and mark the solvent-accessible portions of the biological molecule.

20 Claims, 18 Drawing Sheets

(51) Int. Cl.
*B01J 19/08* (2006.01)
*C12Q 1/6876* (2018.01)
*G01N 1/28* (2006.01)
*G01N 33/487* (2006.01)
*G01N 33/68* (2006.01)
*H01J 49/00* (2006.01)

(56) References Cited

U.S. PATENT DOCUMENTS

2004/0096581 A1* 5/2004 Yashiro ............. H01J 37/32009
 427/248.1
2006/0121515 A1* 6/2006 Otomo ............... C12N 15/1003
 435/6.14
2011/0042560 A1* 2/2011 Ouyang ................ H01J 49/105
 250/282

OTHER PUBLICATIONS

Ke et al, Plasma Process. Polym, vol. 10, pp. 731-739 (2013).*
Zhang Y, et al., (2015) An improved fast photochemical oxidation of proteins (FPOP) platform for protein therapeutics. J Am Soc Mass Spectrom 26(3):526-529.
Klinger AL, et al. (2014) A synchrotron-based hydroxyl radical footprinting analysis of amyloid fibrils and prefibrillar intermediates with residue—fic resolution. Biochemistry 53(49):7724-7734.
Mazzeo, A. et al., Stability Studies for Biologics, Chapter in the Handbook of Stability Testing in Pharmaceutical Development. Springer New York, 2009. pp. 353-369.
Kogelschatz, "Collective phenomena in volume and surface barrier discharges", J. of Physics, 257 012015 (2010).
Bohon J, et al., (2014) Synchrotron X-ray footprinting on tour. J Synchrotron Radiat 21(Pt1):24-31.
Choudhury, F, et al., Fluorophore-based sensor for oxygen radicals in processing plasmas, Journal of Vacuum Science & Technology A 33, 061305 (2015).
Perni, S., et al., 2007. Probing bactericidal mechanisms induced by cold atmospheric plasmas with *Escherichia coli* mutants. Applied Physics Letters, 90 (7), article 073902.
Attri, P., et al. "Influence of reactive species on the modification of biomolecules generated from the soft plasma." Scientific Reports 5.8221:1. 2015.
International Search Report and Written Opinion for PCT/US2017/033621, dated Sep. 11, 2017, 13 pages.

* cited by examiner

METHODS, SYSTEMS, AND COMPOSITIONS FOR STUDYING SOLVENT ACCESSIBILITY AND THREE-DIMENSIONAL STRUCTURE OF BIOLOGICAL MOLECULES

CROSS-REFERENCE TO RELATED APPLICATIONS

This application is related to, claims priority to, and incorporates herein by reference in its entirety U.S. Provisional Patent Application No. 62/338,699, filed May 19, 2016.

STATEMENT REGARDING FEDERALLY FUNDED RESEARCH

This invention was made with government support under MCB1410164 and CBET1066231 awarded by the National Science Foundation and DE-FG02-88ER13938 awarded by the US Department of Energy. The government has certain rights in the invention.

BACKGROUND

Existing methods of interrogating a biological system can derive significant amounts of information. Examples of existing methods include methods for determining an organism's genome, exome, transcriptome, proteome, and metabolome.

The genome can be solved in order to determine an organism's genetic material, typically in the form of DNA (though RNA serves a similar purpose in a subset of organisms). The genome can include all of the genes stored within the genetic material. The exome is a part of the genome that is formed by exons.

The transcriptome refers to the level of expression of mRNA for a cell, a group of cells, or an entire organism. The transcriptome contains some information regarding the environment for a particular cell line, because the mRNA expression products can vary based on environmental conditions.

The proteome refers to the populations of proteins expressed in a cell, a group of cells, or an entire organism. The proteome also contains information regarding the environment for a particular cell line, because protein expression can vary based on environmental conditions.

The metabolome refers to the population of small-molecules present in a biological sample. The metabolome contains additional and different information regarding the environment for a particular cell line, because small-molecule generation and consumption can vary based on environmental conditions.

Beyond all of the above lies an area that has yet to be effectively or efficiently probed, namely the "conformatiome", which refers to the conformational information for any or all of the biological molecules in a given biological sample. The conformatiome ideally provides conformational information regarding various biological molecules in their native and unaltered conformational state.

Current methods that claim to probe conformational structural information suffer from one or more of the following problems. First, some methods require crystallization of a sample (such as x-ray crystallography) or other manipulation that does not present the biological molecule in its native state. Second, some methods require the addition of non-native chemical species to a sample in order to provide species for tagging a sample. One example is fast photochemical oxidation of proteins (FPOP), which requires the addition of hydrogen peroxide to oxidize biological molecules. The addition of hydrogen peroxide may alter the conformational state of the biological molecules being studied. Third, some methods require immensely expensive equipment. For example, the aforementioned FPOP requires use of an excimer laser, which is an expensive instrument. Other methods, such as synchrotron-based hydroxyl radical footprinting, can involve use of multi-million dollar facilities such as a synchrotron.

A need exists for inexpensive systems and fast methods for studying the conformatiome, without the need to introduce the biological molecule(s) in question to foreign substances that might alter their structure.

SUMMARY

The present disclosure overcomes the aforementioned drawbacks by presenting methods, systems, compositions of matter, and kits relating to plasma-induced oxidation of biological molecules.

In one aspect, this disclosure provides a method of modifying a biological molecule located in a sample. The sample can be contacted by a fluid or enclosed within a confined space. The sample or fluid can contain a plurality of marker radical precursors. The method can include one or more of the following steps: a) generating a plasma in the fluid and/or generating the plasma within the sample, the plasma in the fluid having at least a portion of the plasma within 1 cm of the sample, thereby converting one or more of the plurality of marker radical precursors into one or more marker radicals; and b) waiting a length of time sufficient for the one or more marker radicals to interact with the biological molecule, thereby modifying the biological molecule.

In another aspect, this disclosure provides a method of modifying a plurality of biological molecules located in a plurality of samples. The plurality of samples can be contacted by a fluid or isolated in a plurality of confined spaces. The plurality of sample or the fluid can contain a plurality of marker radical precursors. The method can include one or more of the following steps: a) generating a plasma or a plurality of plasmas in the fluid, the plasma or the plurality of plasmas in the fluid having at least a portion of the plasma or the plurality of plasmas within 1 cm of each of the plurality of samples, or generating a plurality of plasmas within the plurality of samples, thereby converting one or more of the plurality of marker radical precursors into one or more marker radicals; and b) waiting a length of time sufficient for one or more of the plurality of marker radicals to interact with the plurality of biological molecules, thereby modifying the plurality of biological molecules.

In yet another aspect, the present disclosure provides a method of determining if a portion of a biological molecule is accessible to a solvent. The biological molecule and the solvent can be contained in a sample. The sample can be contacted by a fluid or enclosed within a confined space. The sample or the fluid can contain a marker radical precursor. The method can include one or more of the following steps: a) oxidizing, by way of a plasma that introduces marker radicals to the sample, the biological molecule; b) subsequent to step a), assessing whether the portion of the biological molecule was oxidized by the oxidizing of step a), wherein the presence of oxidizing indicates that the portion is accessible to the solvent and the absence of oxidizing indicates that the portion is inaccessible to the solvent; and c) generating a report indicating whether the portion is accessible to the solvent or inaccessible to the solvent.

In a further aspect, the present disclosure provides a method of assessing a biological sample containing one or more biological molecules having one or more solvent accessible portions and one or more solvent inaccessible portions. The method can include one or more of the following steps: a) acquiring a first subsample and a second subsample of the biological sample, the first subsample and the second subsample containing substantially equivalent concentrations of the one or more biological molecules; b) introducing a cleavage factor into the second subsample of the biological sample, the cleavage factor configured to alter the one or more biological molecules to expose at least a portion of the solvent inaccessible portions to solvent; c) oxidizing, by way of a plasma that introduces marker radicals to the first subsample and the second subsample, the one or more biological molecules in the first subsample and the second subsample; d) subsequent to step c), assessing a difference in oxidization levels between the one or more biological molecules in the first subsample and the second subsample, thereby identifying at least a portion of the one or more solvent inaccessible portions; and e) generating a report indicating the identification of the at least a portion of the one or more solvent inaccessible portions.

In yet another aspect, the present disclosure provides a system for modifying a biological molecules. The system can include a sample chamber, a ground electrode, a dielectric, a plasma electrode, a plasma electrode positioning system, a power supply, and a control system. The sample chamber can be configured to contain a sample including a biological molecule. The sample chamber can include a chemically and biologically inert inner surface. The dielectric can separate the sample chamber from the ground electrode. The control system can be in electronic communication with the power supply, the ground electrode, and the plasma electrode. The control system can be configured to utilize electrical power from the power supply with the plasma electrode and the ground electrode to generate a plasma from the plasma source point. The plasma can be configured to generate marker radicals suitable for oxidizing the biological molecule.

In a further aspect, the present disclosure provides a system for modifying a biological molecule. The system can include a sample chamber, a plasma jet, a plasma jet positioning system, a power supply, and a control system. The sample chamber can be configured to contain a sample including a biological molecule. The sample chamber can have a chemically and biologically inert inner surface. The plasma jet can be configured to generate a plasma and direct the plasma into the sample chamber. The control system can be in electronic communication with the power supply and the plasma jet. The control system can be configured to utilize electrical power from the power supply with the plasma jet to generate a plasma and direct the plasma into the sample chamber. The plasma can be configured to generate marker radicals suitable for oxidizing the biological molecule.

In an additional aspect, the present disclosure provides a composition of matter. The composition of matter can include a biological molecule and at least one marker radical precursor in a liquid sample and a plasma within the liquid sample. The plasma can be configured to convert the at least one marker radical precursor into a marker radical.

In yet a further aspect, the present disclosure provides a composition of matter. The composition of matter can include a synthetic biological molecule configured to have a predictable response to plasma-induced oxidation.

In another additional aspect, the present disclosure provides a kit. The kit can include a reference sample having a known response to plasma-induced oxidation and information regarding the known response.

BRIEF DESCRIPTIONS OF THE DRAWINGS

DETAILED DESCRIPTION

Figure 1:
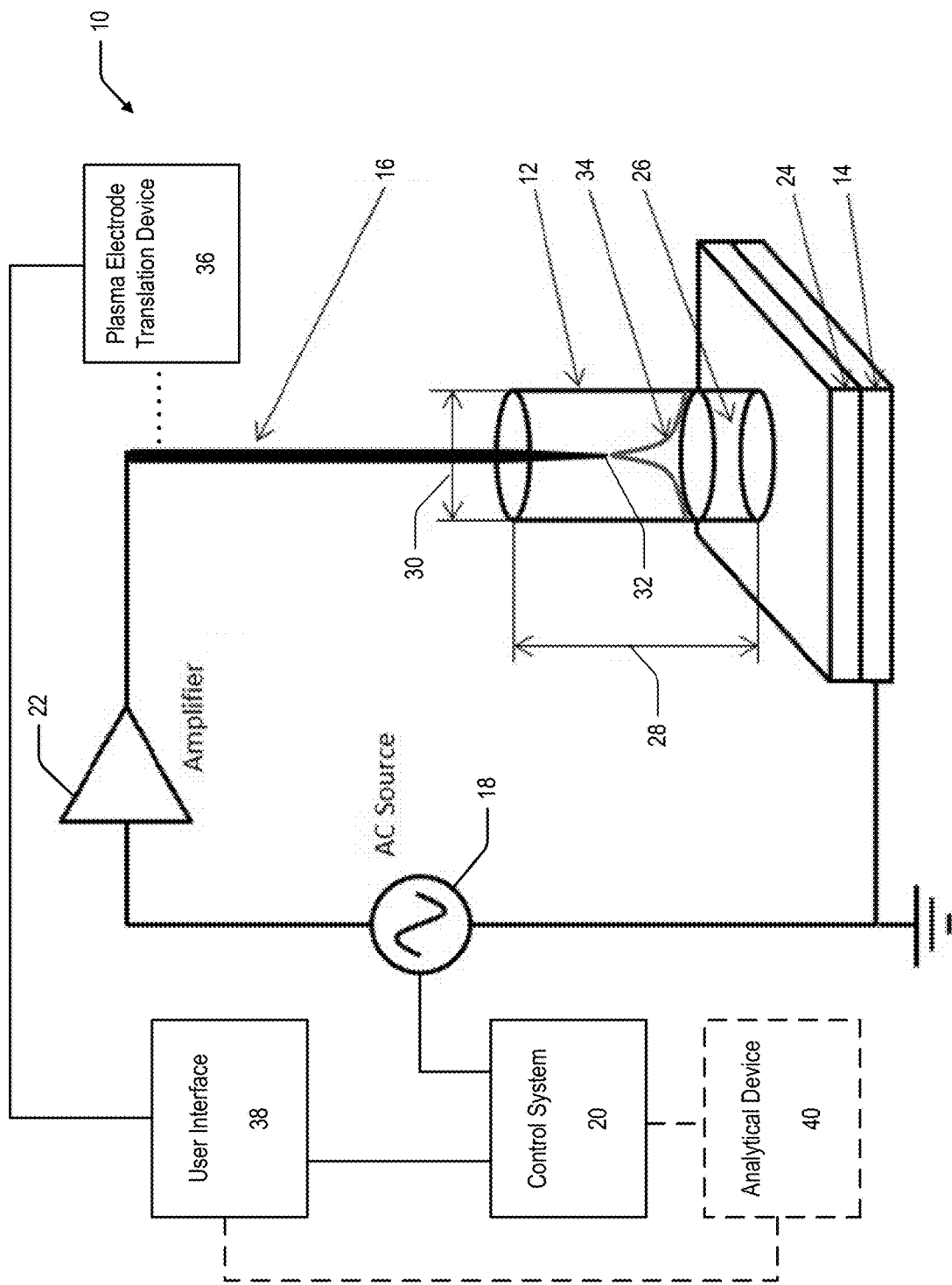
FIG. 1 is a system according to an aspect of the present disclosure.

Before the present invention is described in further detail, it is to be understood that the invention is not limited to the particular embodiments described. It is also understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

Specific structures, devices and methods relating to modifying biological molecules are disclosed. It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. When two or more ranges for a particular value are recited, this disclosure contemplates all combinations of the upper and lower bounds of those ranges that are not explicitly recited. For example, recitation of a value of between 1 and 10 or between 2 and 9 also contemplates a value of between 1 and 9 or between 2 and 10.

The various aspects may be described herein in terms of various functional components and processing steps. It should be appreciated that such components and steps may be realized by any number of hardware components configured to perform the specified functions.

Methods

This disclosure provides a variety of methods. It should be appreciated that various methods are suitable for use with other methods. Similarly, it should be appreciated that various methods are suitable for use with the systems and compositions described elsewhere herein. When a feature of the present disclosure is described with respect to a given method, that feature is also expressly contemplated as being useful for the other methods, the systems, and the compositions described herein, unless the context clearly dictates otherwise.

The methods of the present disclosure generally emerge from a discovery of a new process for modifying biological molecules. This new process involves the generation of a plasma, which itself generates marker radicals (for example, hydroxyl radicals) that can oxidate various substituents on the biological molecule. The oxidation of biological molecules using hydroxyl radicals is generally known and the present disclosure represents an improvement in this process.

In one aspect, this disclosure provides a method of modifying a biological molecule. The biological molecule can be located in a sample. The sample can be contacted by a fluid or enclosed within a confined space. The method can include: a) generating a plasma in the fluid within a distance of the sample or generating the plasma within the sample; and b) waiting a length of time. The plasma can have a nearest point to the sample at a distance of up to 1 cm, including but not limited to, up to 5 mm, up to 3 mm, up to 1 mm, up to 100 µm, up to 10 µm, or up to 1 µm. In certain aspects, the plasma can contact the sample. In certain aspects where the plasma is generated via an electrode, the plasma can be generated by an electrode that is positioned relative to the sample at a distance of up to 3 cm, including but not limited to, a distance of up to 1 cm, or a distance of up to 3 mm. A person having ordinary skill in the art will appreciate that these distances can be scaled up or down by, for example, using a larger or smaller voltage or changing the frequency of plasma pulses.

The generating of step a) can thereby convert one or more of the plurality of marker radical precursors into one or more marker radicals. Examples of the marker radical include, but are not limited to, a hydroxyl radical (.OH), a hydrogen radical (H.), a nitrite or nitrogen dioxide radical (.NO$_2$), a nitrate radical (.NO$_3$), a peroxide radical (.OOH), other radicals known to those having ordinary skill in the art as being generated by a plasma interacting with a radical precursor, combinations thereof, and the like. Examples of the marker radical precursor include, but are not limited to, a hydroxyl radical precursor, such as water or hydrogen peroxide, a hydrogen radical precursors, such as hydrogen gas, a nitrite or nitrogen dioxide radical precursor, such as nitrite or nitrogen dioxide, a nitrate radical precursor, such as nitrate, a peroxide radical precursor, such as hydrogen peroxide, other precursors known to those having ordinary skill in the art to be converted into a radical by interacting with a plasma, combinations thereof, and the like. The length of time can be a length of time sufficient for the one or more marker radicals to interact with the biological molecule. This interaction can modify the biological molecule.

Without wishing to be bound by any particular theory, the generating a plasma in the fluid can involve converting marker radical precursors in the fluid into marker radicals, which then diffuse or are somehow otherwise transported into the sample. Without wishing to be bound by any particular theory, the generating a plasma within the sample can involve converting marker radical precursors in the sample into marker radicals, which diffuse within the sample and then interact with the biological molecules. In certain aspects, the generating a plasma in the fluid or within the sample can include generating a plasma within both the fluid and the sample.

In certain aspects, the generating a plasma step can include generating a plasma from a plasma jet. The principle behind the plasma jet is described in greater detail below, but briefly, the plasma jet involves generating a plasma in a confined space and subsequently using gas flow to project the generated plasma toward a target (in this case, toward the sample).

The generating a plasma step can include generating a single plasma pulse or a sequence of plasma pulses.

In certain aspects, the plasma can be generated by a voltage of between 1 V and 1 MV, including but not limited to, a voltage of between 500 V and 100 kV, between 1 kV and 50 kV, or between 5 kV and 15 kV. As with the distances disclosed above, these voltages can be scaled up or down depending on the specific operational parameters.

In aspects utilizing a sequence of plasma pulses, the operational parameters in this paragraph can be utilized. The plasma pulses can have a pulse width in a range of between 1 ps and 1 ms, including but not limited to, a pulse with in a range of between 500 ps and 100 µs or between 1 ns and 10 µs. The sequence of plasma pulses can have a frequency in a range of between 1 Hz and 100 GHz, including but not limited to, a frequency in a range of between 10 Hz and 100 MHz, or between 1 kHz and 10 kHz. The sequence of plasma pulses can be generated for a total length of time in a range of between 1 ns and hours to days, including but not limited to, a total length of time in a range of between between 100 ns and 20 minutes, between 1 µs and 1 hour, between 1 ms and 30 minutes, between 1 s and 10 minutes, or between 30 s and 5 minutes. The aforementioned pulse width, frequency, and total length of time parameters for a sequence of plasma pulses can vary depending on the lifetime of the marker radicals being produced, the concentration of the target biological molecule, the size of the target biological molecule, the concentration of the marker radical precursor, the stability of the target biological molecule in the presence of varying concentrations of the marker radicals, and/or the extent of modification and/or destruction of the biological molecule that is desired.

In certain aspects, the plasma generating step can be configured to generate a concentration of marker radicals with the sample. The concentration of marker radicals is at its highest immediately following the plasma and decays over time as the marker radicals interact with biological molecules, interact with other components within the sample, and/or naturally decay over time due to recombination processes. In certain aspects, the generating a plasma step can be configured to provide a peak concentration of marker radicals in the sample that can be between 50 nM and 800 µM, including but not limited to, a peak concentration of marker radicals in the sample of between 500 nM and 800 nM, between 5 µM and 8 µM, or between 50 µm and 80 µm. In certain aspects, the generating a plasma step can be configured to provide an average concentration of marker radicals in the sample of between between 50 nM and 800 µM, including but not limited to, a peak concentration of marker radicals in the sample of between 500 nM and 800 nM, between 5 µM and 8 µM, or between 50 µm and 80 µm. In certain aspects, the average concentration can be a fraction or percentage of the values provided based on the "on" time of the plasma, including but not limited to, 75%, 50%, 40%, 30%, 20%, or 10% of the values provided. The average concentration can be measured for the length of time during which the plasma or the sequence of plasma pulses is generated plus a length of time of about 5 seconds, 10 seconds, 30 second, or 1 minute.

In certain aspects, the generating a plasma step can elevate a temperature of the sample by an amount less than an amount that would begin denaturation of the biological molecule or the plurality of biological molecules. If the plurality of biological molecules have different temperatures at which they denature, then the generating a plasma step can elevate the temperature of the sample by an amount less than an amount that would begin denaturation of the biological molecule having the lowest denaturation temperature. For purposes of this aspect of the disclosure, denaturation can refer to denaturation of quaternary, tertiary, or secondary structure.

In certain aspects, the generating a plasma step can elevate a temperature of the sample by less than 50° C., including but not limited to, less than 5° C., or less than 0.5° C. In certain aspects, the generating a plasma step can elevate a temperature of the sample to a temperature of less than 73.5° C., including but not limited to, a temperature of less than 28.5° C., or a temperature of less than 23.5° C.

In certain aspects, the generating a plasma step can transfer an amount of energy per unit volume to the sample of less than 60 MJ/µL, including but not limited to, an amount of energy per unit volume to the sample of less than 180 MJ/µL, or less than 360 MJ/µL.

In certain aspects, the method can be performed on a sample having a volume of between 1 µL and 400 L, including but not limited to, a volume of between 10 µL and 100 mL, or a volume between 50 µL and 200 µL.

In aspects where the sample is contacted by a fluid, the fluid can be a gaseous feedgas containing marker radical precursor in a concentration range of between 0.01 wt % and 99.99 wt %, including but not limited to, a concentration range of between 10% and 99.9%, or between 90% and 99%. The gaseous feedgas can be air, oxygen, nitrogen, argon, helium, xenon, krypton, carbon tetrafluoride, hydrogen, combinations thereof, and the like.

In aspects where the marker radical precursor is located in the sample, the sample can contain marker radical precursor in a concentration range of between 0.01 wt % and 99.99 wt %, including but not limited to, a concentration range of between 10% and 99.9%, or between 90% and 99%.

The methods of modifying a biological molecule can be extended to modify a plurality of biological molecules. This can be done in at least two ways. First, a single sample can contain multiple biological molecules. Second, a plurality of samples, each containing at least one biological molecule, can undergo the methods described herein. For this second approach involving a plurality of samples, the aspects of the methods described with respect to a single sample, such as volume for example, can be applicable to each of the plurality of samples.

The sample can be a biological sample that contains within it one or more biological molecules or the sample can be a sample that is prepared to include the biological molecule, such as a protein sample that is dissolved in a buffer solution.

In certain aspects, the biological molecule can be selected from the group consisting of a nucleic acid molecule, a protein, a lipid, a biological metabolite, and combinations thereof.

In certain aspects, the sample can be selected from the group consisting of blood, blood plasma, urine, saliva, lymph, tears, sweat, cerebrospinal fluid, amniotic fluid, aqueous humour, vitreous humour, bile, breast milk, cerumen, chyle, chime, endolymph, perilymph, exudates, feces, female ejaculate, gastric acid, gastric juice, mucus, pericardial fluid, peritoneal fluid, pleural fluid, pus, rheum, sebum, serious fluid, semen, smegma, sputum, synovial fluid, vaginal secretion, vomit, living bacterial cultures, living tissue or eukaryotic cell cultures, and combinations thereof. In certain aspects, the sample can be selected from the group consisting of eukaryotic intracellular fluid, eukaryotic extracellular fluid, prokaryotic intracellular fluid, prokaryotic extracellular fluid, homogenized tissue or cells, homogenized tissue or cell culture, homogenized plant tissue, and combinations thereof. In certain aspects where the sample is extracellular fluid, the extracellular fluid can be selected from the group consisting of intravascular fluid, interstitial fluid, lymphatic fluid, transcellular fluid, plant apoplastic or vascular fluid, excess nutrient medium from prokaryotic or eukaryotic in vitro growth, and combinations thereof. In certain aspects where the sample is living bacterial, tissue, or eukaryotic cell cultures, the cultures can be any species of prokaryotic organism, any mammalian tissue or cell culture, any culturable species of eukaryotic organism, or combinations thereof. In certain aspects, the sample can be any living organism or sub-component of an organism, such as one or more cells, that can be suitable positioned in the systems described herein and/or suitable for use in the methods described herein.

In certain aspects, the sample can comprise one or more biological molecules and a buffer solution. In certain aspects, the buffer solution can include or be a phosphate buffered saline solution, tris(hydroxymethyl)aminomethane (tris), tris hydrochloric acid, ammonium bicarbonate, 4-(2-hydroxyethyl)-1-piperazineethanesulfonic acid (HEPES), 3-(N-morpholino)propanesulfonic acid (MOPS), 2-(N-morpholino)ethanesulfonic acid (MES), 2,2-Bis(hydroxymethyl)-2,2',2"-nitrilotriethanol (bis-tris), N-(2-Acetamido) iminodiacetic acid (ADA), piperazine-N,N'-bis(2-ethanesulfonic acid) (PIPES), N-(2-Acetamido)-2-aminoethanesulfonic acid (ACES), 3-(N-morpholinyl)-2-hydroxypropanesulfonic acid sodium salt (MOPSO), 1,3-bis(tris(hydroxymethyl)methylamino)propane (bis-tris propane), N,N-Bis(2-hydroxyethyl)-2-aminoethanesulfonic acid (BES), 2-[[1,3-dihydroxy-2-(hydroxymethyl)propan-2-yl]amino]ethanesulfonic acid (TES), 3-(Bis(2-hydroxyethyl)amino)-2-hydroxypropane-1-sulfonic acid (DIPSO), 3-[[1,3-dihydroxy-2-(hydroxymethyl)propan-2-yl]amino]-2-hydroxypropane-1-sulfonic acid (TAPSO), 2 amino-2-(hydroxymethyl)-1,3-propanediol, piperazine-1,4-bis(2-hydroxypropanesulfonic acid) dihydrate (POPSO), 3-[4-(2-

Hydroxyethyl)-1-piperazinyl]propanesulfonic acid (HEPPS), N-(2-Hydroxy-1,1-bis(hydroxymethyl)ethyl)glycine (TRICINE), glycylglycine (GLY-GLY), 2-(Bis(2-hydroxyethyl)amino)acetic acid (BICINE), N-(2-hydroxyethyl)piperazine-N'-(4-butanesulfonic acid) (HEPBS), 3-[[1,3-dihydroxy-2-(hydroxymethyl)propan-2-yl]amino] propane-1-sulfonic acid (TAPS), 2-amino-2-methyl-1,3-propanediol (AMPD), N-(1,1-Dimethyl-2-hydroxyethyl)-3-amino-2-hydroxypropanesulfonic acid (AN/IPSO), N-cyclohexyl-2-aminoethanesulfonic acid (CHES), N-cyclohexyl-2-hydroxyl-3-aminopropanesulfonic acid (CAPSO), 1-amino-2-methyl-1-propanol (AMP), N-cyclohexyl-3-aminopropanesulfonic acid (CAPS), 4-(cyclohexylamino)-1-butanesulfonic acid (CABS), Lysogeny broth (LB) or other nutrient growth media, anything defined as a 'biological buffer', a biologically or physiologically-relevant salt, combinations thereof, and the like. In certain aspects, the buffer solution can have a pH value of between 1 and 14, including but not limited to, a pH of between 3 and 9, or a pH of between 4 and 8.

The operational parameters of the methods described above can be utilized by a person having ordinary skill in the art to introduce a desired amount of oxidation to a biological molecule. In addition, the operational parameters can be utilized by a person having ordinary skill in the art to induce this oxidation with a minimal amount of damage to the biological molecule. On the other hand, the operational parameters can be utilized by a person having ordinary skill in the art to induce this oxidation under conditions that cause a desired amount of damage to the biological molecule. It should be appreciated that various sorts of information can be realized from methods that induce no damage and various different sorts of information can be realized from methods that induce controlled damage and/or complete damage.

The control of the level of oxidation and the amount of damage can be monitored using a control sample having a predictable, known response to certain ideal operational parameters. For example, the cytochrome C experiments described below in Example 1 could be used as a benchmark for determining if the operational parameters for a certain experiment are appropriate. In certain aspects, the methods described herein can include a step of confirming a set of operational parameters using a control sample having a known response to plasma-induced oxidation.

The methods described above can be utilized to determine structural information about a biological molecule. Biological molecules can include secondary, tertiary, and quaternary structure that precludes solvent interaction with various parts of the biological molecule.

In another aspect, the present disclosure provides a method of determining if a portion of a biological molecule is accessible to a solvent. The method can include the following steps: oxidizing, by way of a plasma that introduces marker radicals to the sample, the biological molecule; subsequent to the oxidizing, assessing whether the portion of the biological molecule was oxidized by the oxidizing of step a), wherein the presence of oxidizing indicates that the portion is accessible to the solvent and the absence of oxidizing indicates that the portion is inaccessible to the solvent; and generating a report indicating whether the portion is accessible to the solvent or inaccessible to the solvent.

In another aspect, this disclosure provides a method of assessing a biological sample containing one or more biological molecules having one or more solvent accessible portions and one or more solvent inaccessible portions. The method can include the following steps: acquiring a first subsample and a second subsample of the biological sample, the first subsample and the second subsample containing substantially equivalent concentrations of the one or more biological molecules; introducing a cleavage factor into the second subsample of the biological sample, the cleavage factor configured to alter the one or more biological molecules to expose at least a portion of the solvent inaccessible portions to solvent; oxidizing, by way of a plasma that introduces marker radicals to the first subsample and the second subsample, the one or more biological molecules in the first subsample and the second subsample; subsequent to the oxidizing, assessing the difference in oxidization levels between the one or more biological molecules in the first subsample and the second subsample, thereby identifying at least a portion of the one or more solvent inaccessible portions; and generating a report.

The oxidizing of these methods can be achieved by the methods described elsewhere herein.

The introducing a cleavage factor step can be used to prompt a predictable change in structure in the one or more biological molecules. Using this predictable change in structure as a baseline of comparison, comparing the oxidation levels of biological molecules not subject to the cleavage factor with those that were subject to the cleavage factor can provide information about the solvent accessibility.

In some aspects, the cleavage factor can expose all of the solvent inaccessible portions of the one or more biological molecules to solvent. For example, a protein can be digested into individual amino acids, which are all accessible to solvent, in which case the digested protein would have all portions accessible to solvent, and thus oxidation, and the undigested protein would have only its normally solvent accessible portions accessible to solvent.

The cleavage factor can be Trypsin (bovine), Chymotrypsin (bovine), Endoproteinase Asp-N (*Pseudomonas fragi*), Endoproteinase Arg-C (mouse submaxillary gland), Endoproteinase Glu-C (V8 protease) (*Staphylococcus aureus*), Endoproteinase Lys-C (*Lysobacter enzymogenes*), Pepsin (porcine), Thermolysin (*Bacillus thermo-proteolyticus*), Elastase (porcine), Papain (*Carica papaya*), Proteinase K (*Tritirachium album*), Subtilisin (*Bacillus subtilis*), Clostripain (endoproteinase-Arg-C) (*Clostridium histolyticum*), Exopeptidase, Carboxypeptidase A (bovine), Carboxypeptidase B (porcine), Carboxypeptidase P (*Penicillium janthinellum*), Carboxypeptidase Y (yeast), Cathepsin C, Acylamino-acid-releasing enzyme (porcine), Pyroglutamate aminopeptidase (bovine), other cleavage factors known to those having ordinary skill in the art, combinations thereof, and the like.

The assessing steps can involve mass spectrometry analysis, gel electrophoresis, sequencing, such as DNA sequencing, and the like. The oxidizing described herein can change the molecular weight of a portion of a biological molecule. For instance, certain amino acids are susceptible to oxidation by marker radicals. An increase in the molecular weight of a specific amino acid indicates that it was solvent accessible at the time of the oxidizing. As another example, a piece of DNA in vivo can be sheltered from the surrounding environment (for example, by having a protein bound to it), and that piece will not be exposed to the radicals generated as described herein, and thus will not undergo radical cleavage. Thus, pieces of DNA that remain intact and are identified as such can be correlated with being bound by proteins in vivo.

The methods described herein can be useful for a variety of applications, including but not limited to, quality control for biopharmaceuticals. Biopharmaceuticals can be effective in certain cases only if they retain the necessary secondary, tertiary, and/or quaternary structure to allow them to function in a biological environment as intended. Accordingly, during production, throughout transportation, and prior to use, it can be important to confirm that a biopharmaceutical has not lost its intended secondary, tertiary, and/or quaternary structure. The methods described herein provide the means to monitor this structure, and assess the compliance of a biopharmaceutical.

The methods described herein can also be utilized in assessing a disease state in a subject, where the disease state is expressed by a conformational change in one or more biological molecules. For example, if a disease state is expressed by the breaking apart of a protein dimer, the methods of the present disclosure could be used to identify that the contact surfaces between the subunits of the dimer, which are normally not accessible to solvent, have become accessible to solvent. If the methods determine that the contact surfaces are accessible to solvent, then this information could be used to form a diagnosis for the disease state.

The methods described herein can be utilized to study temperature-dependent properties of a sample of interest. For example, kinetics, protein folding, and other temperature-dependent mechanisms of interest can be studied with temperature-dependent deployment of the methods described herein.

The methods described herein can be utilized to determine a rate of modification for components or sub-components within the sample of interest. For example, the methods described herein can compare the rate of oxidation of two different residues on a protein of interest and can make various subsequent deductions based on the differences between those rates, such as determining a level of solvent accessibility.

Systems

This disclosure also provides systems. The systems can be suitable for use with the methods and compositions described herein. When a feature of the present disclosure is described with respect to a given system, that feature is also expressly contemplated as being combinable with the other systems, the methods, and the compositions described herein, unless the context clearly dictates otherwise. In addition, features described below with respect to the aspect of the present disclosure shown in FIG. 1 are applicable to the aspect of the present disclosure shown in FIG. 2, and vice versa, unless the context clearly dictates otherwise. For example, the cooling device 44, sample chamber holder 46, or protective housing 48 and door 50 illustrated in FIG. 2 can be deployed in the context of FIG. 1 without departing from the scope of the present disclosure.

In an aspect, referring to FIG. 1, the disclosure provides a system 10 for modifying a biological molecule. The system 10 for modifying a biological molecule can include a sample chamber 12, a ground electrode 14, a plasma electrode 16, a power supply 18, and a control system 20. The system 10 can also include an amplifier 22 located between the power supply 18 and the plasma electrode 16. The system can include a dielectric 24 located between the sample chamber 12 and the ground electrode 14.

The sample chamber 12 can be configured to receive a sample 26. The sample 26 can be those described elsewhere herein. The sample chamber 12 can have an inner surface that is chemically and/or biologically inert. As used herein, biologically inert refers to a material not impacting the conformational state of one or more biological molecules.

The sample chamber 12 can take various shapes, such as a cylinder, an elliptical cylinder, a cuboid, a frustum of a cone, a frustum of a pyramid (triangular, rectangular, pentagonal, etc.), a prism (triangular, pentagonal, hexagonal, etc.), any suitable shape for holding a liquid sample, any subdivision thereof (for example, a semicylinder), and the like.

The sample chamber 12 can have a height 28 and a width 30 that are configured to provide optimal plasma generation, and subsequent interaction of generated marker radicals. The height 28 can be 0.75 inches and the width 30 can be 0.5 inches, though other sizes of sample chamber 12 are contemplated and appropriate sizes can be determined by a person having ordinary skill in the art.

In some aspects, the sample chamber 12 can have an open top. In some aspects, the sample chamber can have a closed top. In aspects where the sample chamber 12 has a closed top, the sample 26 can entirely fill the sample chamber 12, such that there is no fluid, such as a gas, air, etc., contacting the sample 26 or the sample 26 can fill a portion of the sample chamber 12 with a fluid occupying the remaining portion of the sample chamber 12.

In certain aspects, the sample chamber 12 can be a portion of a microfluidic device and/or channel.

The ground electrode 14 can be composed of a conductive material known to those having ordinary skill in the art. Examples of suitable conductive materials for use in the ground electrode 14 include, but are not limited to, copper, silver, gold, aluminum, iron, graphite, calcium, beryllium, magnesium, rhodium, molybdenum, iridium, tungsten, zinc, cobalt, cadmium, nickel, ruthenium, lithium, osmium, platinum, palladium, selenium, tantalum, columbium, lead, vanadium, tin, titanium, conductive oxides thereof, conductive alloys thereof, conductive polymers, and combinations thereof.

The plasma electrode 16 can be composed of a conductive material known to those having ordinary skill in the art. Examples of suitable conductive materials for use in the plasma electrode 16 include, but are not limited to, the materials listed above as suitable for use in the ground electrode 14.

In some aspects, the plasma electrode 16 can be in close proximity to the sample or can contact the sample. In cases where the plasma electrode 16 is in close proximity to the sample or in contact with the sample, the plasma electrode 16 can be made of a material that is non-contaminating of the sample. A person having ordinary skill in the art will appreciate that the extent to which the plasma electrode 16 is contaminating of the sample is dependent on the properties of the sample. The plasma electrode 16 can be non-contaminating to the samples described elsewhere herein.

The plasma electrode 16 can have a plasma source point 32 that is the point from which the plasma 34 emerges. The plasma electrode 16 can have multiple plasma source points 32.

In certain aspects, the plasma electrode 16 can have a dielectric coating (not illustrated) that can prevent direct contact between the plasma electrode 16 and the sample 26. The dielectric coating can cover at least the plasma source point 32. A person having ordinary skill in the art will appreciate the impact that such a coating might have on the plasma generation properties of the system 10, and can adjust the various aspects of the system 10 to accommodate such a coating while maintaining the overall performance of the system 10.

In certain aspects, the plasma electrode 16 can have the shape of a needle or any shape suitable for producing a plasma 34. The plasma source point 32 can take a shape that is suitable for producing a plasma 34 in accordance with the present disclosure. In certain aspects, the plasma source point 32 can take the shape of a needle tip, a convex rounded surface, a flat surface, multiple needle tips, a disk, a sphere, or other shapes known to a person having ordinary skill in the art to be suitable for generating a plasma 34.

In certain aspects, the plasma 34 can be generated by a plasma generator that does not include electrodes. As one example, a microwave source can be configured to generate a plasma 34 having the properties described elsewhere herein.

In certain aspects, the plasma electrode 16 can be mechanically coupled to a plasma electrode translation device 36. Examples of plasma electrode translation devices 36 include, but are not limited to, 1-, 2-, or 3-dimensional translation stages (manual and motor-driven), a robotic arm, an array of electrodes, and the like.

Also contemplated are systems where the sample chamber 12, the ground electrode 14, and optionally the dielectric 24 are movable relative to the plasma electrode 16 by way of a sample chamber translation device (not illustrated). Examples of sample chamber translation devices include those described above with respect to the plasma electrode translation devices 36.

The control system 20 can include various function generators, programmable controls, pulse generators, voltmeters, ampmeters, light sensors, thermometers, gas pressure sensors, gas flow controllers, fluorimeters, monochromaters, liquid flow meters, liquid flow controllers, timers, or other components that a person having ordinary skill in the art would recognize as useful for the control of various components of the system 10. In some cases, the control system 20 is a computer. The control system 20 can be configured to provide precision control of the time of plasma discharge. The control system 20 can provide millisecond resolution of plasma discharge, such as resolution of greater than 100 ms, greater than 10 ms, or greater than 1 ms.

The system 10 can include a user interface 38. The user interface 38 can be in communication with the control system 20 and/or the electrode translation device 36. The user interface can take the form of a computer, a personal device, such as a tablet or a smart phone, an arrangement of mechanical inputs such as buttons, knobs, switches, and the like, or other means of receiving user input and providing signals to the control system 20 and/or the electrode translation device 36 to operate the system 10.

In certain aspects, the system 10 can have more than one sample chamber 12. In these aspects, the system 10 can also have more than one plasma electrodes 16 in an amount equal to the number of sample chambers 16. For example, the system 10 can have an array of sample chambers 12 similar to a 96-well plate and an array of individual or independent plasma electrodes 16 configured such that each sample chamber 12 has a plasma source point 32 positioned within it for generation of plasmas 34.

In an aspect, the system 10 can be used for assessing a biological sample. The system 10 for assessing the biological sample can optionally include an analytical device 40 capable of determining whether a portion of a biological molecule has been modified by a marker radical. The analytical device 40 can optionally be in electronic communication with the control system 20 and/or the user input 38. The control system 20 can optionally coordinate control of the analytical device 40 along with other aspects of the system 10. The user interface 38 can optionally be used in coordination with the analytical device 40 to control the analytical device and/or to directly receive user inputs for control of the analytical device 40.

In certain aspects, the analytical device 40 can be a mass spectrometer. The mass spectrometer can be a dedicated mass spectrometer configured to detect species of particular relevance. For example, a dedicated mass spectrometer can be configured to detect the mass of oxidized and non-oxidized peptides, for which sequence information localizing the modified amino acids can be obtained, while ignoring other masses.

In certain aspects, the sample chamber 12 can be directly connected to the analytical device 40, so the sample can be processed automatically without requiring a user to transfer the sample to the analytical device. In certain aspects, an automated transfer can occur by way of, for example, a robotic pipette system.

In certain aspects, the system 10 can include a sample hopper for automatically introducing the sample 26 into the sample chamber 12. An example of a sample hopper includes, but is not limited to, an automated pipette positioned above the sample chamber. A person having ordinary skill in the art will appreciate that automation technology that is usable with other technologies, such as gas chromatography, can be usable with the system 10.

By using the automated loading and/or the automated transfer to the analytical device, in combination with the reference samples and kits described below, the system 10 can automatically optimize the operational parameters. For example, the system 10 could have stored in a memory a reference mass spectrum. The system could then automatically introduce a reference sample into the sample chamber, automatically oxidize the reference sample with a set of operational parameters, automatically transfer the oxidized reference sample to a mass spec, automatically acquire a mass spectrum of the reference sample, the compare the acquired mass spectrum with the stored reference mass spectrum. The system could repeat this process and vary the operational parameters using an optimizing routine until the acquired mass spectrum substantially matches the stored reference mass spectrum.

As used herein, a "ground electrode" refers to an individual ground electrode or a plurality of ground electrodes that grounded substantially equivalently to one another. For example, a plurality of copper electrodes that are all electronically connected to a single ground can be considered a ground electrode in the context of this disclosure. For clarity, reference to a ground electrode includes any number of individual ground electrodes.

Figure 2:
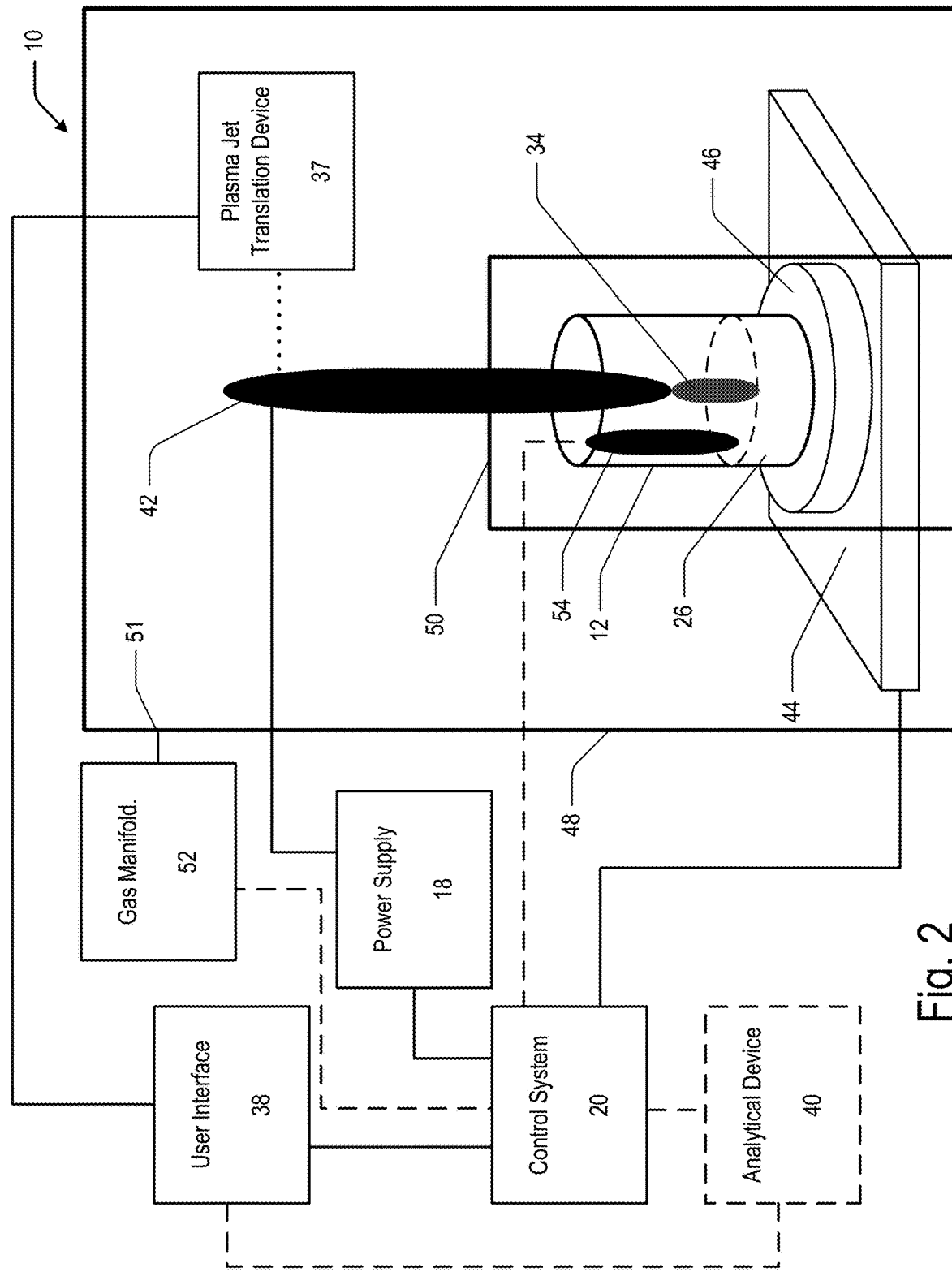
FIG. 2 is a system according to an aspect of the present disclosure.

Referring to FIG. 2, the system 10 is illustrated with modifications that are compatible with and swappable with features illustrated in FIG. 1. Features shown in FIG. 2 and described above with respect to FIG. 1 will not be reiterated here for efficiency sake, but are deployed in the same and/or similar context described above. Should such features require adaptation to be used in the context of FIG. 2, a person having ordinary skill in the art would understand how to accommodate such adaptations. In an aspect, referring to FIG. 2, the disclosure provides a system 10 including a plasma jet 42. The system 10 can include a plasma jet translation device 37 configured to physical manipulate the plasma jet 42 in order to precisely deliver a plasma 34 emerging from the plasma jet 42. The system 10 can include a cooling device 44 configured to thermally cool the sample 26 within the sample chamber 12. The system can include a sample chamber holder 46 configured to receive the sample chamber 12. The system 10 can include a protective housing 48. The protective housing 48 can include a door 50. The system 10 can include a gas manifold 52. The system 10 can include a temperature sensor 54.

As used herein, the term "plasma jet" refers to a device that generates a plasma within a first space and propels the generated plasma toward a target by way of movement of a gas and the shaping of the plasma jet. Persons having ordinary skill in the plasma generating arts will recognize that the plasma jet can take various forms without departing from the scope of the present disclosure. In one example, the plasma jet 42 can be a glass tube through which a fluid having marker radical precursors, as described above, flows. The glass tube can be surrounded by electrodes, in some cases coiled electrodes, that are configured to generate a plasma 34 within the glass tube. The flow rate of the fluid can then be adjusted to propel the plasma 34 out of the glass tube and toward the sample 26. The glass tube can have a shape to facilitate reproducible directing of the plasma 34. The plasma jet 42 can have feedgas controls known to those having ordinary skill in the art and can be controlled by the control system 42. The plasma jet 42 can also have the capacity to deploy sheath gases for control of directionality, size, and shape of the plasma 34. A non-limiting example of a commercially-available plasma jet is the PlasmaJet®, available commercially from Plasma Surgical, Inc. headquartered in Roswell, Ga.

The advantages of using a plasma jet 42 can include, but are not limited to, positional flexibility, increased control of the plasma 34, and other advantages that would be appreciated to those of skill in the art. As one example, use of a plasma jet 42 can facilitate the use of a larger sample chamber 12. In this example, the plasma jet 42 could be deployed to "scan" (for example, a raster scanning motion) across a large area surface of the sample 26 and introduce the plasma 34 to different areas of the sample 26.

In some cases, the plasma jet 42 can have turbulence associated with its function. This turbulence can be used advantageously to aid in mixing of the sample 26.

The cooling device 44 can be a convective cooling device known to a person having ordinary skill in the art. Example of suitable cooling devices 44 include, but are not limited to, a liquid flow-through cooling device, a Peltier cooler, and the like. The cooling device 44 can be controlled by the control system 20. Although not illustrated, it should be appreciated that the cooling device 44 could also be a heating device or a cooling and heating device.

The sample chamber holder 46 can be configured to receive the sample chamber 12 and can thus have a size and shape that is relative to the size and shape of the sample chamber 12. In some cases, the sample chamber holder 46 can have a recessed cavity configured to receive the sample chamber 12. In some cases, the sample chamber holder 46 can have a flat surface on which the sample chamber 12 rests. In certain cases, where the sample chamber 12 has a cylindrical shape, the sample chamber holder 46 can have a cylindrical cavity configured to receive the sample chamber. The sample chamber holder 46 can be made of a material that is thermally conductive, such as ceramic. The sample chamber holder 46 can be electrically insulating.

The protective housing 48 can be hermetically sealed. The door 50 of the protective housing 48 can have an automatic locking mechanism (not illustrated). The automatic locking mechanism can be in electronic communication with and controlled by the control system 20. The automatic locking mechanism can function by locking the door 50 when the system 10 is in use and unlocking the door 50 when the system 10 is inactive. The protective housing 48 can have an inlet 51 for receiving gas for the purpose of controlling the environment within the protective housing. The gas manifold 52 can be coupled to the inlet and can control the atmospheric composition within the protective housing 48. The gas manifold 52 can be manually controlled or can be automatically controlled, optionally by the control system 20. The protective housing 48 can be transparent. The protective housing 48 can be made of plexiglass.

The temperature sensor 54 can be positioned near the sample chamber 12, within the sample chamber 12, near the sample 26, and/or within the sample 26. Multiple temperature sensor 54 can be used. The temperature sensor 54 can be a thermometer, a thermocouple, or any other device known to those having ordinary skill in the art to be useful to measuring temperature in a gas and/or liquid. The temperature sensor 54 can optionally be in communication with the control system 20. The temperature measured by the temperature sensor 54 can be utilized as feedback to control the system 10 and specifically to control the plasma 34 and/or the cooling device 44.

The power supply 18 can include and utilize a flyback transformer, thus providing high voltage performance at a lowered cost.

The control system 20 can receive feedback regarding the number of plasma pulses that have been introduced to the sample and can further control the system 10 based off that feedback.

In some cases, the sample 26 can have a layer of oil (not illustrated) atop the sample 26 in order to minimize evaporation and/or turbulence.

Compositions of Matter

This disclosure provides compositions of matter.

In one aspect, a composition of matter can comprise a biological molecule in a liquid sample and a plasma within the sample. The liquid sample can include at least one marker radical precursor. The plasma can be configured to convert the marker radical precursor into a marker radical.

In one aspect, a composition of matter can comprise a biological molecule in a liquid sample that is contacted by a fluid and a plasma within the liquid sample and/or the fluid. The liquid sample and/or the fluid can include at least one marker radical precursor. The plasma can be configured to convert the marker radical precursor into a marker radical.

In certain aspects of the aforementioned compositions of matter, the composition can include a plurality of marker radical precursors and some portion of the precursors have been converted into marker radicals, so the composition includes the plasma, marker radical precursors, and marker radicals.

In one aspect, a composition of matter can comprise a synthetic biological molecule configured to have a predictable response to plasma-induced oxidation. The synthetic biological molecule can have a pre-determined mass and/or a pre-determined sequence. The synthetic biological molecule can be configured to be selectively oxidized a pre-determined number of times, such as 1 time, 2 times, 3 times, and so on, up to n times. The synthetic biological molecule can be configured to be selectively oxidized on a particular residue, such as a specific amino acid, or on multiple particular residues. The synthetic biological molecule can be configured to be selectively oxidized by a particular radical marker.

The synthetic biological molecule can be configured to be selectively oxidized on a particular residue that is solvent accessible under certain conditions and solvent inaccessible under other conditions. For example, the particular residue can be solvent accessible at a first temperature, pH, salinity, or other parameter, and solvent inaccessible at a second temperature, pH, salinity, or other parameter.

In certain aspects, a composition of matter can comprise a mixture of synthetic biological molecules configured to have pre-determined properties, such as those set forth above with respect to the synthetic biological molecules, and/or a predictable response to plasma-induced oxidation.

In certain aspects, the compositions of matter can be utilized as standards for benchmarking performance of the systems and methods described herein.

Kits

This disclosure provides kits.

In one aspect, a kit can include a reference sample and information that allows the reference sample to be useful in identifying properties of a biological molecule in accordance with one or more of the methods described above. The reference sample can have a known response to plasma-induced oxidation. The information can include the known response. For example, the information can be a known mass spectrum for an optimally plasma-induced oxidation of a reference sample can be stored on a memory.

Experimentalists will appreciate that protein samples can be precious. Accordingly, the kits of the present disclosure can allow a user to tune the system to the appropriate settings, thereby only risking destruction of a less precious reference sample. For example, a reference sample having a known response to the methods described above and information describing that known response can be used to optimize the operational parameters of the system, then the optimized operational parameters can be used with the sample of interest itself.

In one aspect, the kit can be used to determine if a system is appropriately configured.

The reference sample can include the features of the samples described elsewhere herein, so long as the response to plasma-induced oxidation is known to some degree.

The information can be in the form of a reference mass spectrum or a catalog of reference mass spectra.

Example 1

Labeling Cytochrome C

A system as shown in FIG. 1 was used to generate radicals in a protein solution. The plasma was produced as follows. A low voltage a.c. source generated a variable frequency signal that was in the audio-frequency range. This signal was fed into a Trek amplifier (available commercially from Trek, Inc., Lockport, N.Y.) to produce a high-voltage signal at the same frequency up to 30 kHz. The output of the Trek amplifier was then fed to a nickel needle that was placed above the protein solution in a glass tube. The glass tube had a height of 0.75 inches and a diameter of 0.5 inches. The tube was sealed to a thin sheet of glass (0.0625 inches thick) that served as the dielectric barrier. A copper electrode was placed on the opposite side of the glass dielectric and was connected to the other (grounded) side of the signal generator. The plasma was formed in microsecond bursts whenever the voltage between the needle and the copper electrode exceeded a particular value that was dependent on the voltage magnitude and the frequency of the signal generator. The plasma was generated in the air above the protein solution and extended into the liquid itself.

Figure 3:
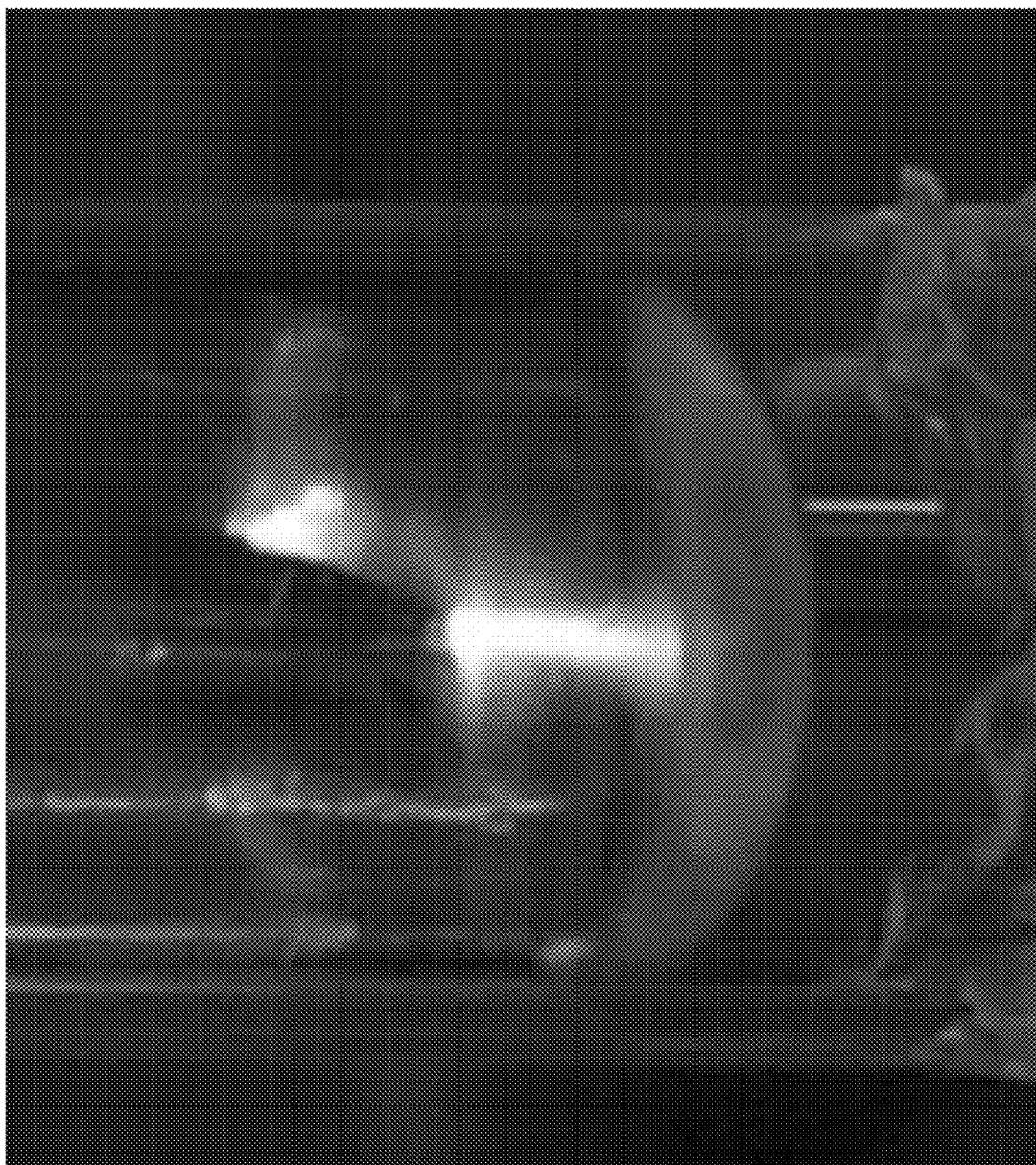
FIG. 3 is an image of a plasma according to an aspect of the present disclosure.
Figure 4:
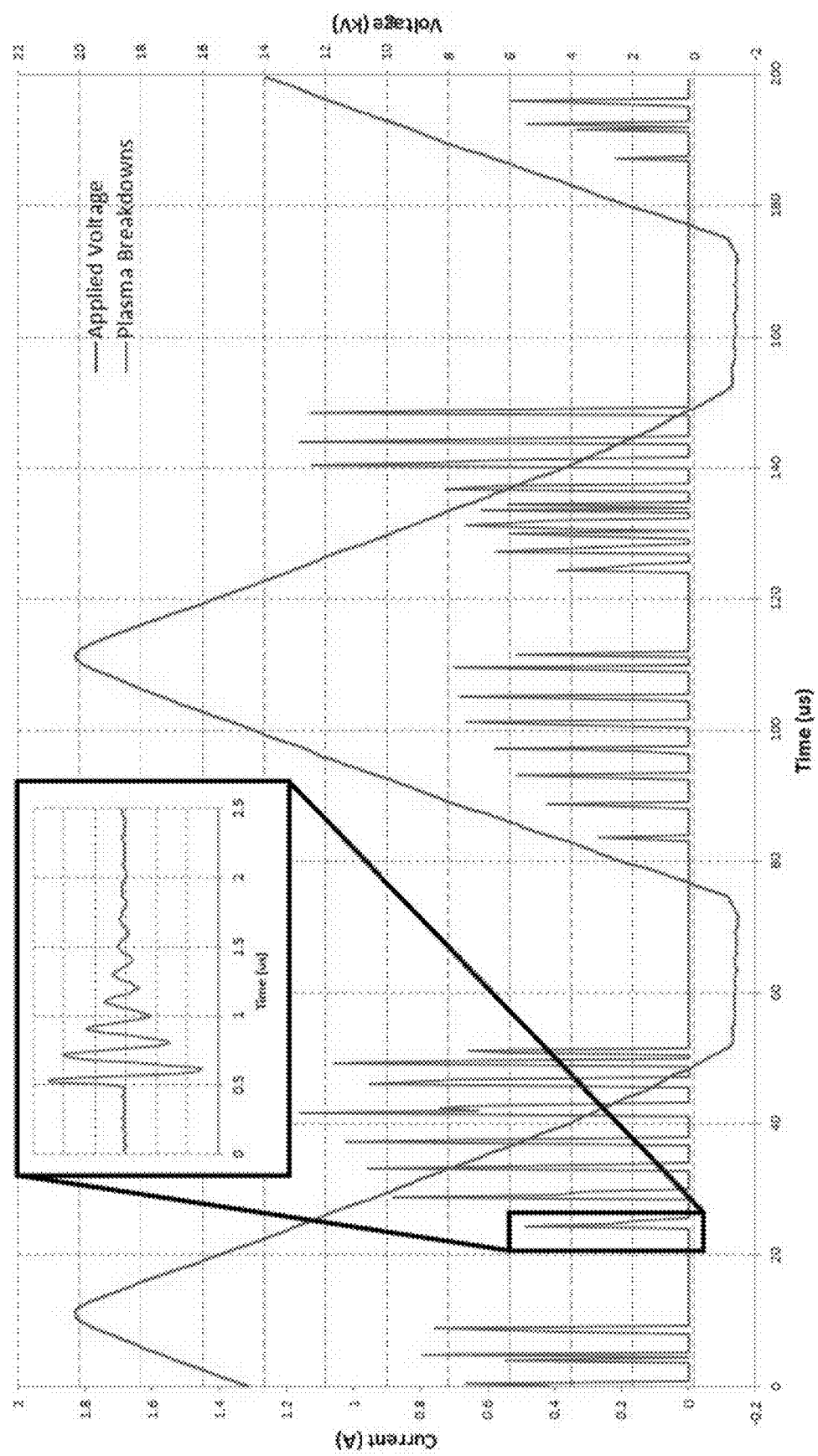
FIG. 4 is a plot of the voltage and current across a discharge, as described in Example 1.

A photograph of the dielectric-barrier discharge that resulted is shown in FIG. 3. A plot of the voltage and current across the discharge is shown in FIG. 4, where the voltage is labeled U and the current is labeled I. The plot shows the times where the breakdown occurred and the plasma was generated. The voltage spiked up and current swung between positive and negative values, with a pulse width of 3-4 μs.

Figure 5:
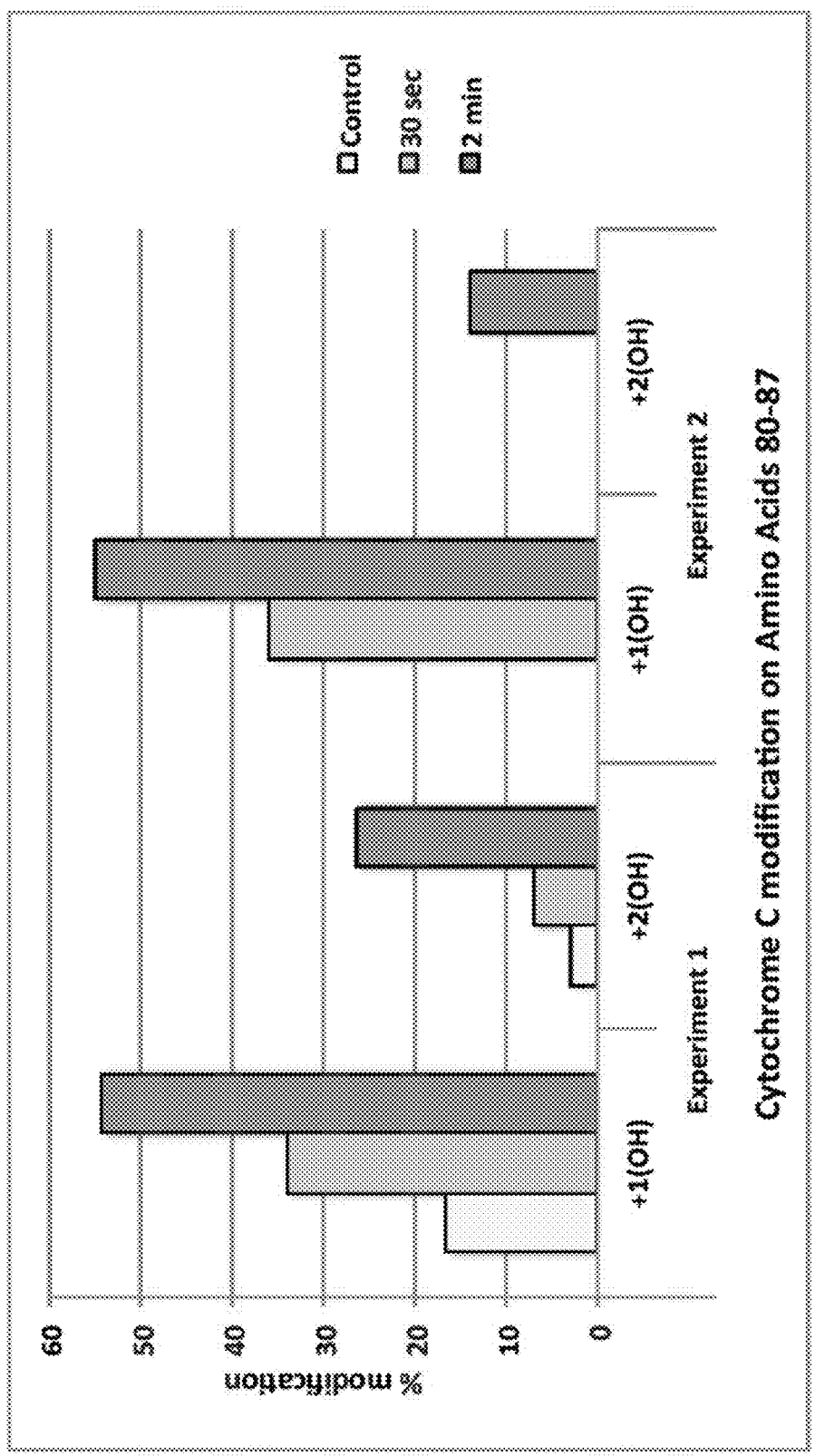
FIG. 5 is a plot showing relative modification of a biological molecule, as described in Example 1.

A purified protein, cytochrome C, was used in the protein solution to illustrate the protein labeling capabilities of this method. Cytochrome C is a model protein that has historically been benchmarked by other methods, including the synchotron-based method described in the background section. To demonstrate the effectiveness of the method, cytochrome C in a lightly buffered salt solution at a concentration of 50 μM was tested under the following conditions: no plasma exposure; 30 seconds of plasma exposure; and 2 minutes of plasma exposure. The experiments were conducted twice, independently, and analyzed using two different, complementary mass spectrometric techniques. The results have been condensed into FIG. 5, which illustrates that increasing plasma exposure time increased modification on a specific region of cytochrome C. These experiments validated that the methods described above are both dose-dependent and reproducible.

Example 2

Labeling Bovine Serum Albumin

A system as shown in FIG. 1 was used to generate radicals in a protein solution with the same operational parameters described in Example 1.

A purified bovine serum albumin (BSA) in a lightly buffered salt solution at a concentration of 10 μM was tested under the following conditions: no plasma exposure; 30 seconds of plasma exposure; and 1 minute of plasma exposure. Four different peptides within BSA were modified by the method in a dose-dependent fashion.

Figure 6:
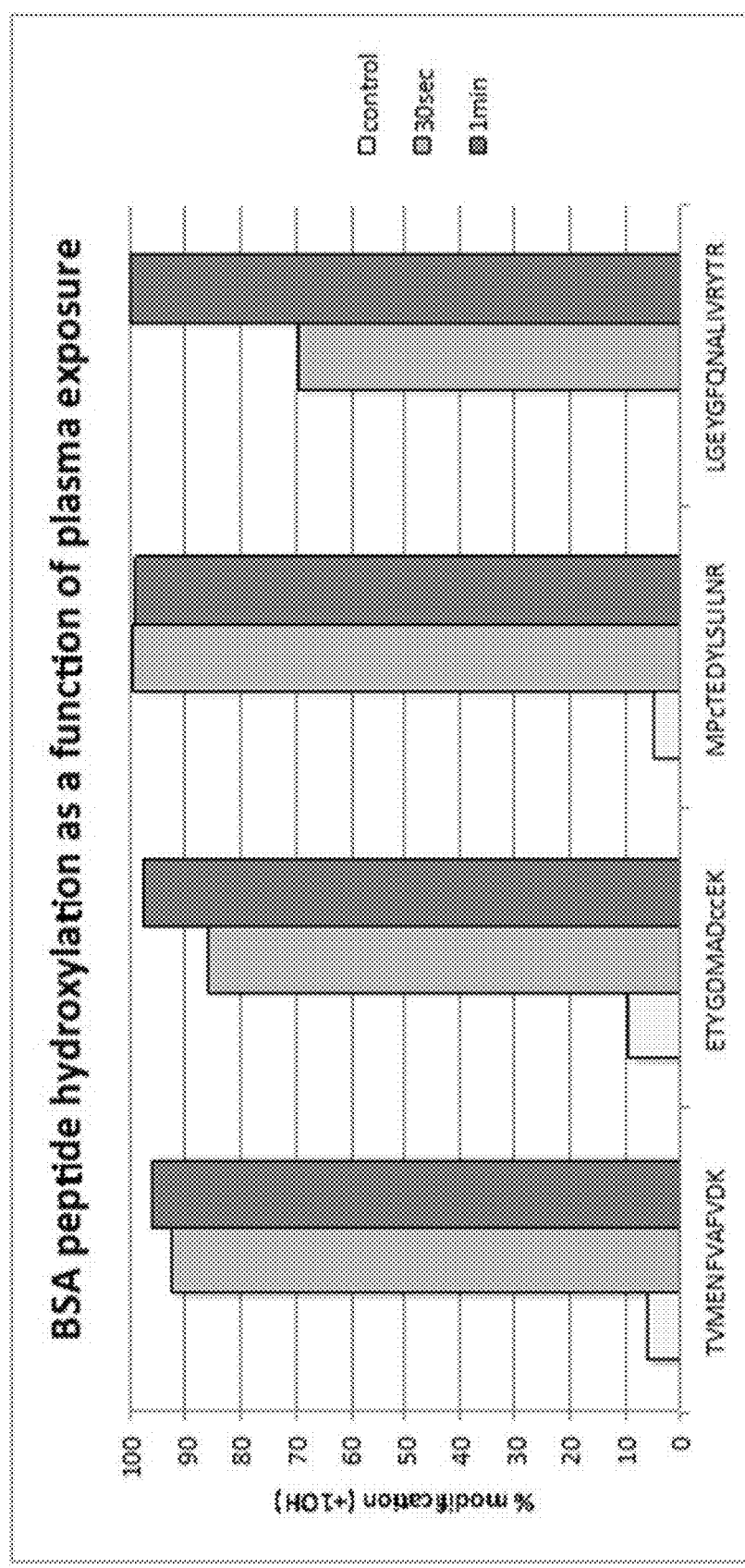
FIG. 6 is a plot showing percent modification of a biological molecule, as described in Example 2.

Referring to FIG. 6, a plot shows the percent modification for the four different peptides under the three different conditions. In combination with Example 1, this Example illustrates the effectiveness of the systems and methods at labeling proteins at different concentrations, labeling proteins that are different in size, and labeling proteins with different physiochemical properties.

Example 3

Breakdown of DNA in Size-Dependent and Exposure-Dose-Dependent Fashion

Figure 7:
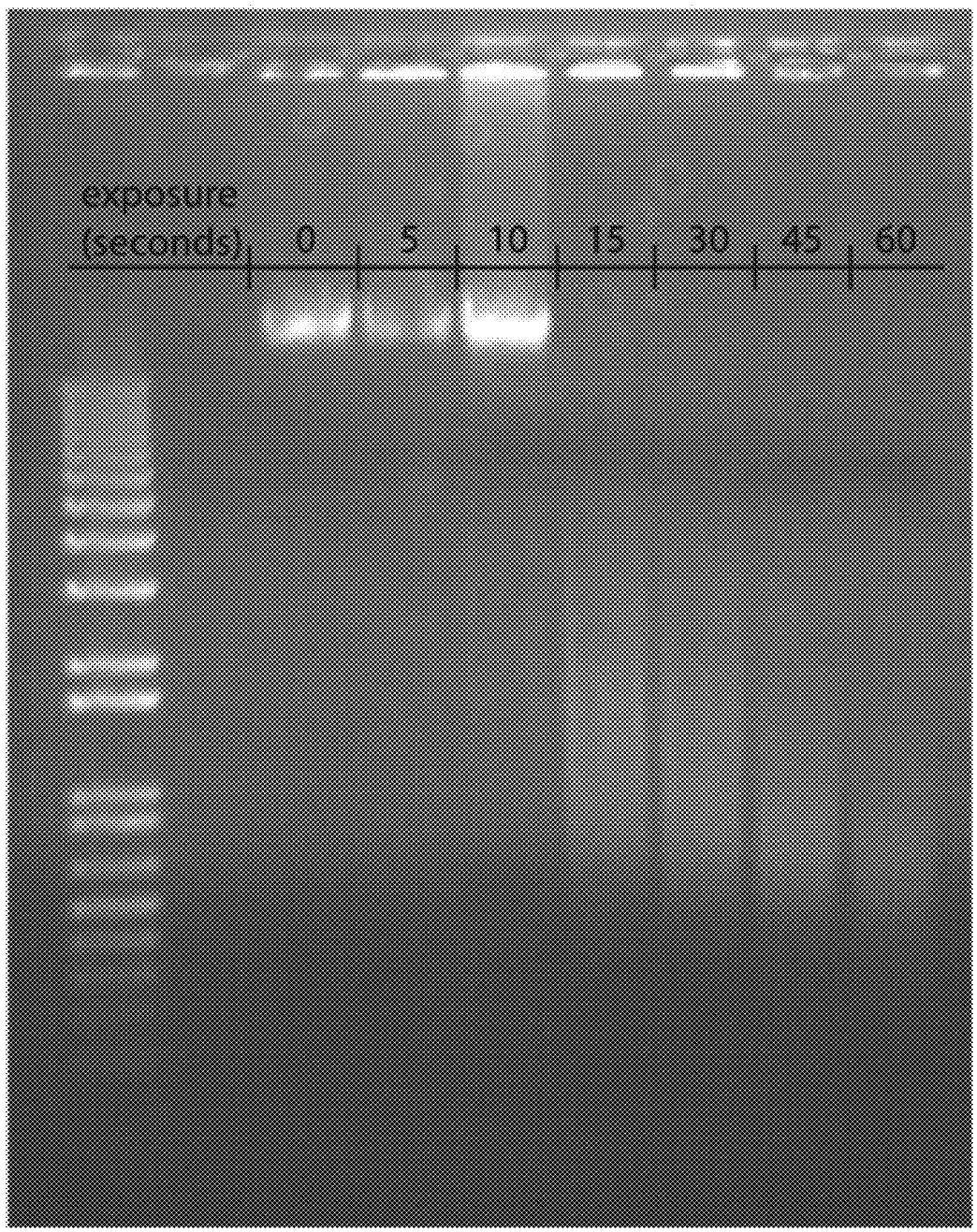
FIG. 7 is an image of an electrophoresis gel illustrating breakdown of DNA, as described in Example 3.

A purified lambda phage genomic DNA sample in water was utilized as a sample with an experimental setup similar to the one shown in FIG. 1 and the experimental parameters described in Example 1. The lambda phage genome contains 48,500 base pairs and is linear. Samples were exposed to no plasma, 5 seconds, 10 seconds, 15 seconds, 30 seconds, 45 seconds, and 60 seconds of plasma. Referring to FIG. 7, an electrophoresis gel run with the DNA samples after the plasma exposure is shown. The samples with no exposure, 5 seconds exposure, and 10 seconds exposure were largely unmodified. The samples with 15 seconds, 30 seconds, 45 seconds, and 60 seconds exposure produced a smear in the gel. The smear represents many different DNA breakdown products, which resulted from hydroxyl radicals cleaving DNA non-specifically, thus leading to pieces having a variety of different sizes. The shifting of the smear as the exposure time increases illustrates that the breakdown products decrease in size as exposure time increases.

Figure 8:
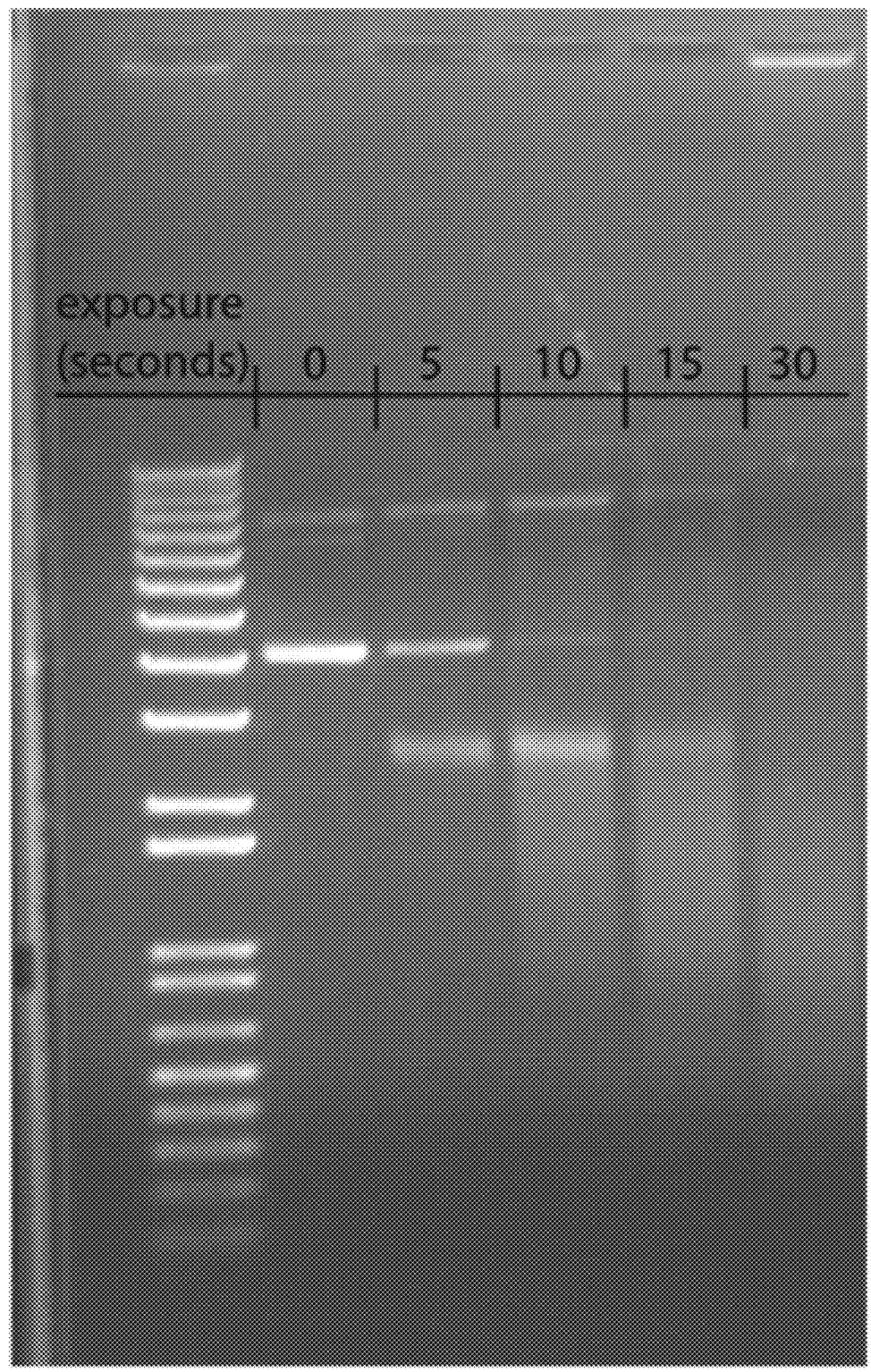
FIG. 8 is an image of an electrophoresis gel illustrating breakdown of DNA, as described in Example 3.

A 7500 base pair plasmid (circular DNA) was exposed to the same conditions for no exposure, 5 seconds exposure, 10 seconds exposure, 15 seconds exposure, and 30 seconds exposure. Referring to FIG. 8, an electrophoresis gel run with the DNA samples after the plasma exposure is shown. In this case, less overall exposure time was necessary to begin breaking down this DNA compared with the lambda phage genomic DNA, although similar results overall were observed.

Example 4

Protein Labeling in Intact/Live Cells

Figure 9:
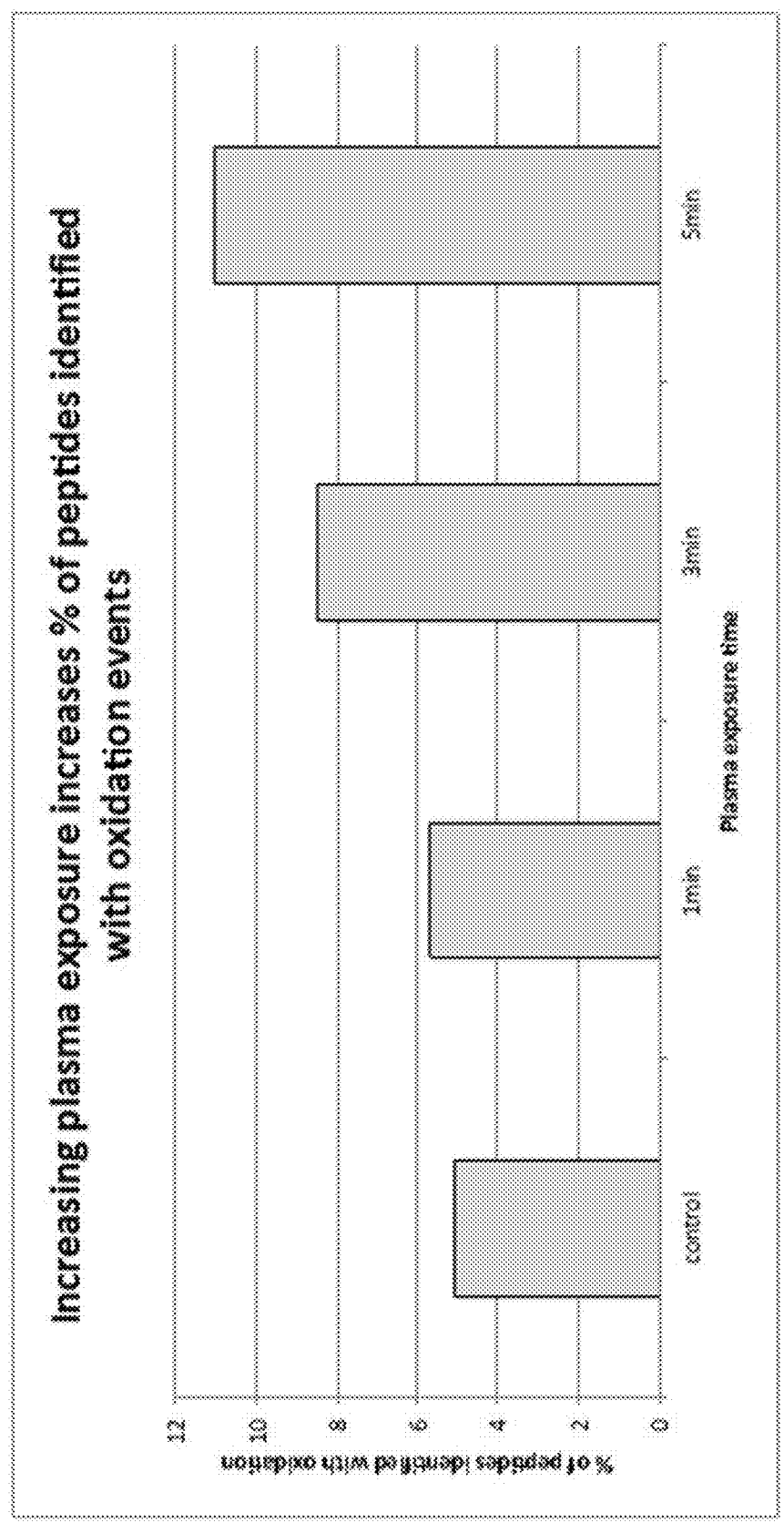
FIG. 9 is a plot showing percent modification of a biological molecule within a cell, as described in Example 4.

Live *E. coli* were exposed to the plasma conditions described in Example 1. The samples were exposed to no plasma, 1 minute of plasma exposure, 3 minutes of plasma exposure, and 5 minutes of plasma exposure. No significant decrease in *E. coli* viability was observed as a result of the plasma exposure. All of the peptides for which sequence information was derived post-mass spectral analysis were examined, and a dose-dependent increase in the percentage of peptides that were identified which contain at least one oxidation event. The results are summarized in FIG. 9.

Figure 10:
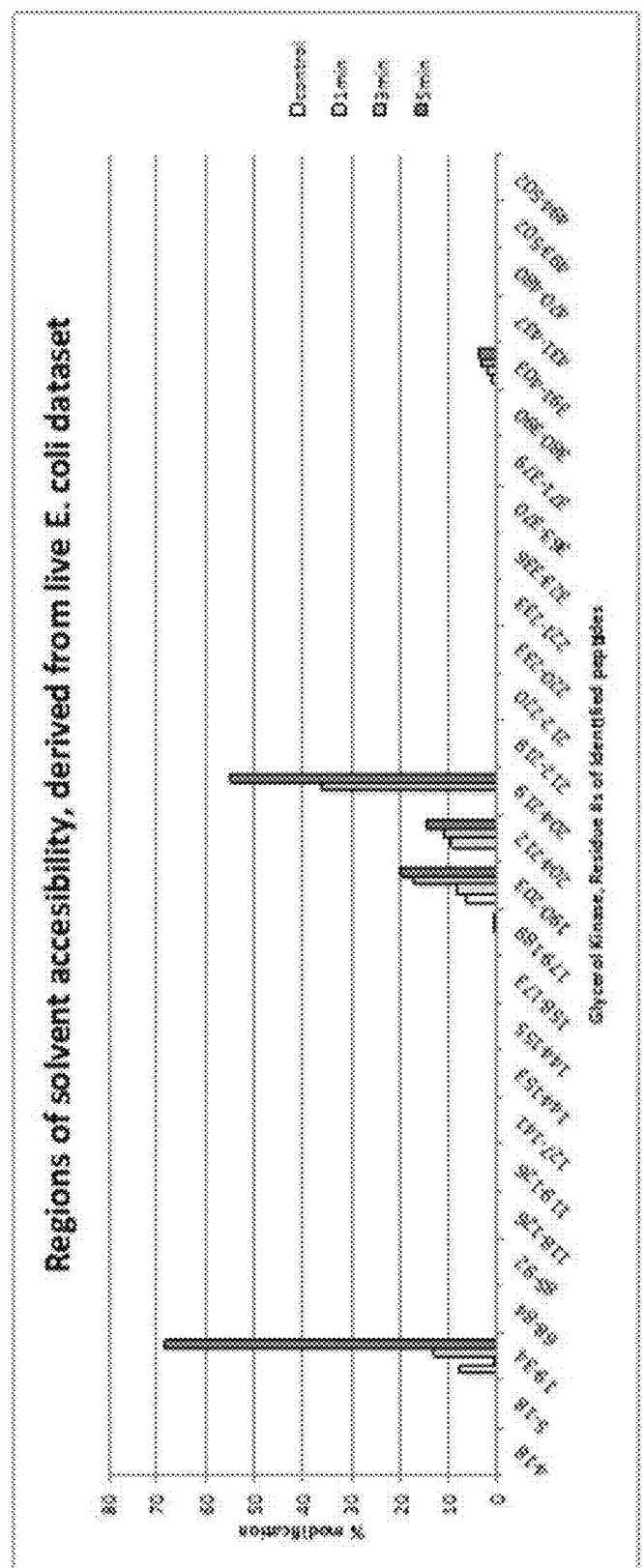
FIG. 10 is a plot showing percent modification of specific portions of a specific biological molecule within a cell, as described in Example 4.

Glycerol kinase, a single protein from *E. coli*, was isolated from the proteomic background for analysis. Referring to FIG. 10, a plot of percent modification versus position within the protein is shown. The plot illustrates that modification selectively occurred in specific regions of the protein, in particular, the regions that are exposed to solvent.

Example 5

Conformational Sensitivity to Oxidation

The experimental parameters of Example 1 were reiterated on two samples: 1) a solution containing intact cytochrome C; and 2) a solution containing cytochrome C that was denatured by first proteolyzing down to peptides. Both solutions were exposed to the plasma for the same length of time. The labeling was more extensive for the denatured cytochrome C when compared with the intact cytochrome C. This result provides evidence that conformational information can be derived from the systems and methods disclosed herein.

Example 6

Comparison of Native Versus Digested Bovine Serum Albumin

Figure 11:
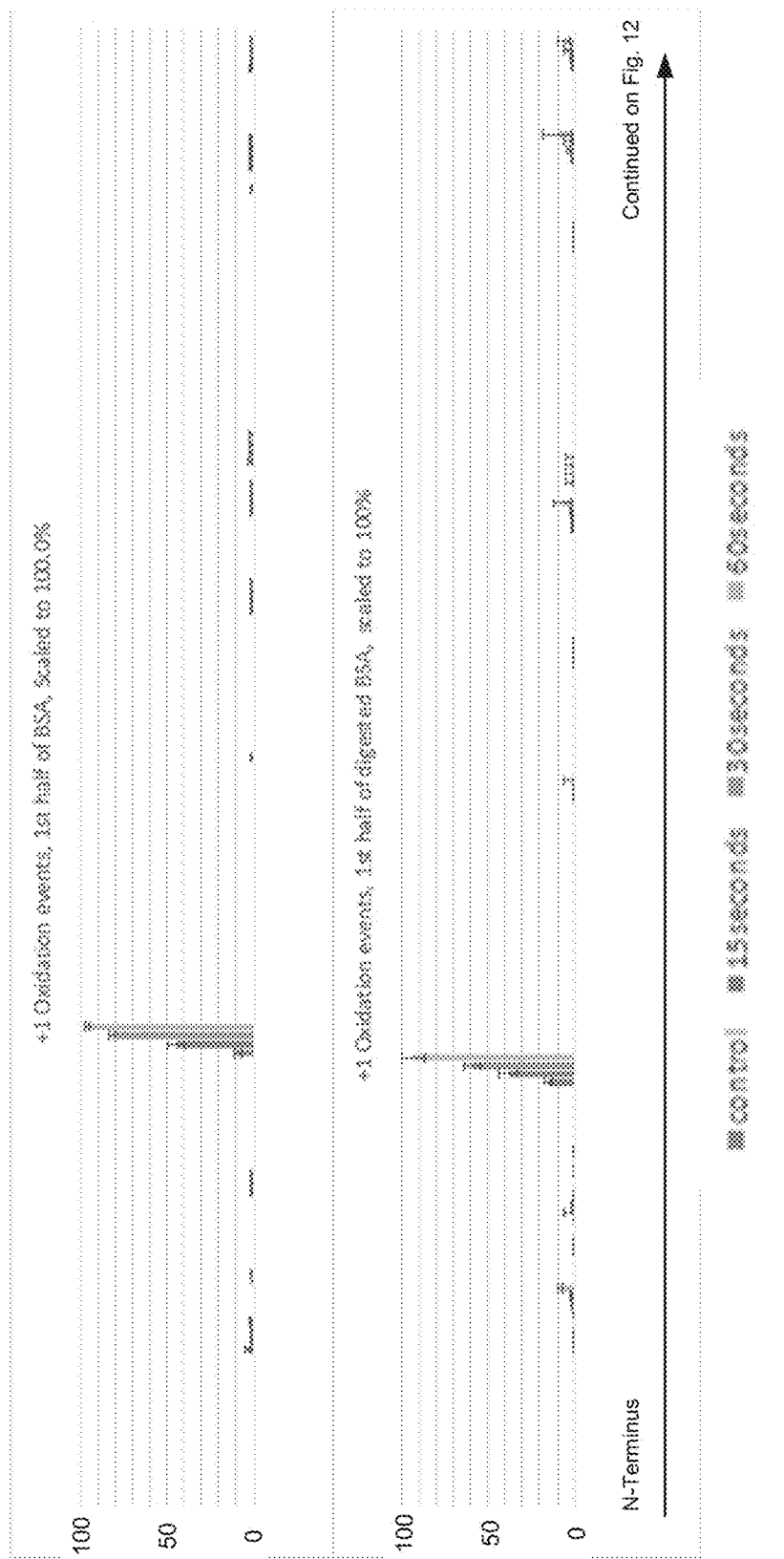
FIG. 11 is a pair of plots of oxidation of undigested and digested bovine serum albumin, as described in Example 6.
Figure 12:
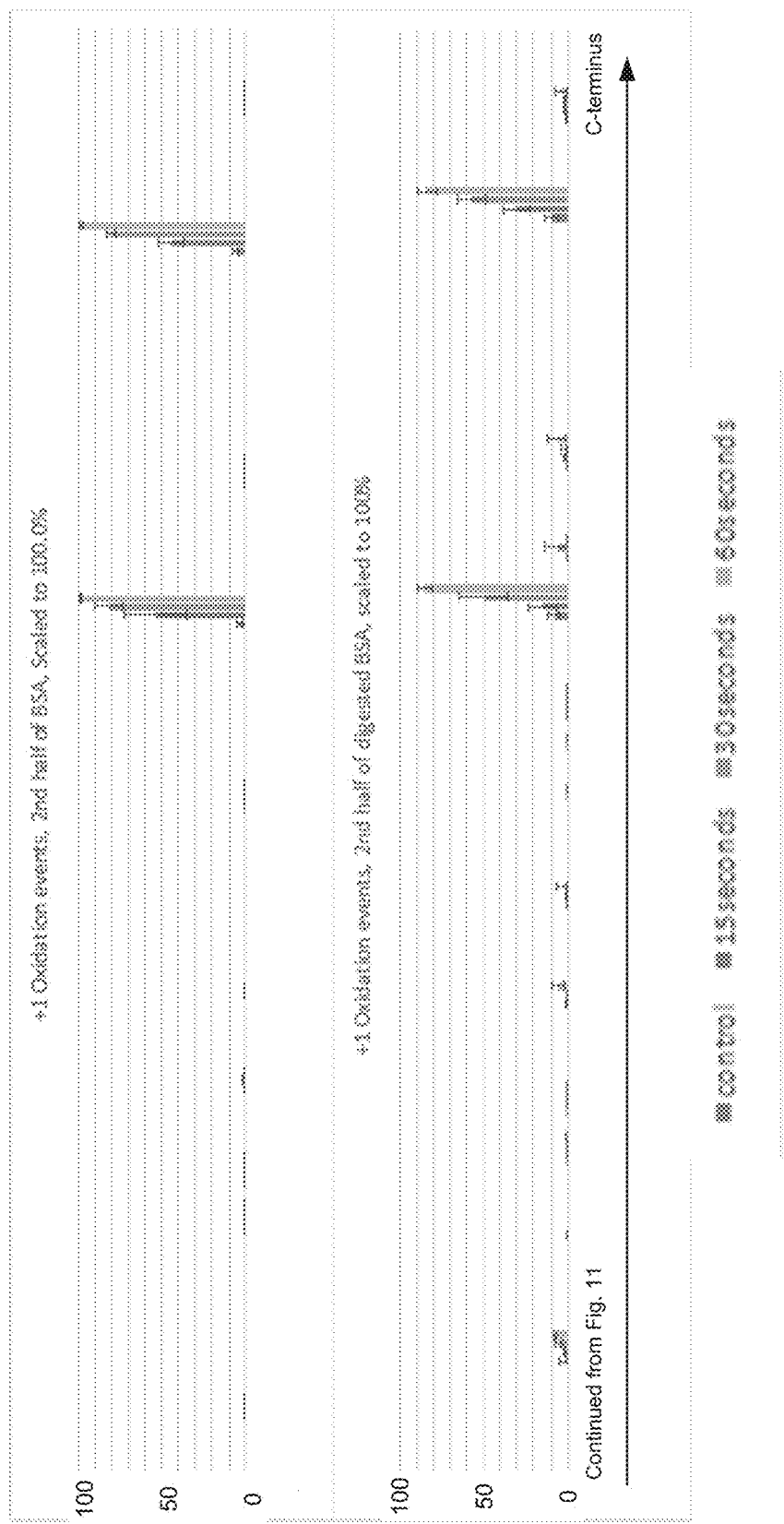
FIG. 12 is a pair of plots of oxidation of undigested and digested bovine serum albumin, as described in Example 6.
Figure 13:
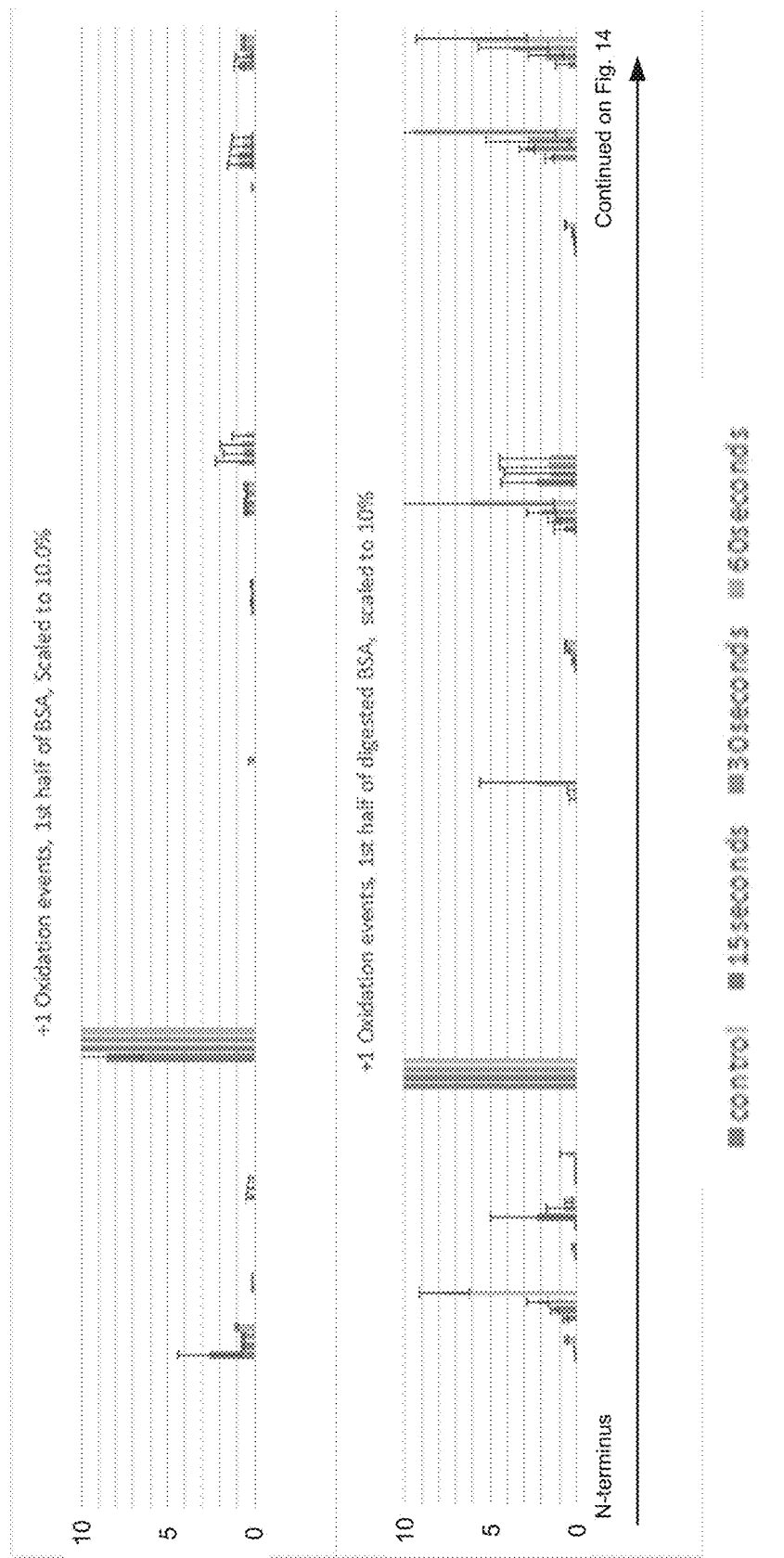
FIG. 13 is a pair of plots of oxidation of undigested and digested bovine serum albumin, as described in Example 6.
Figure 14:
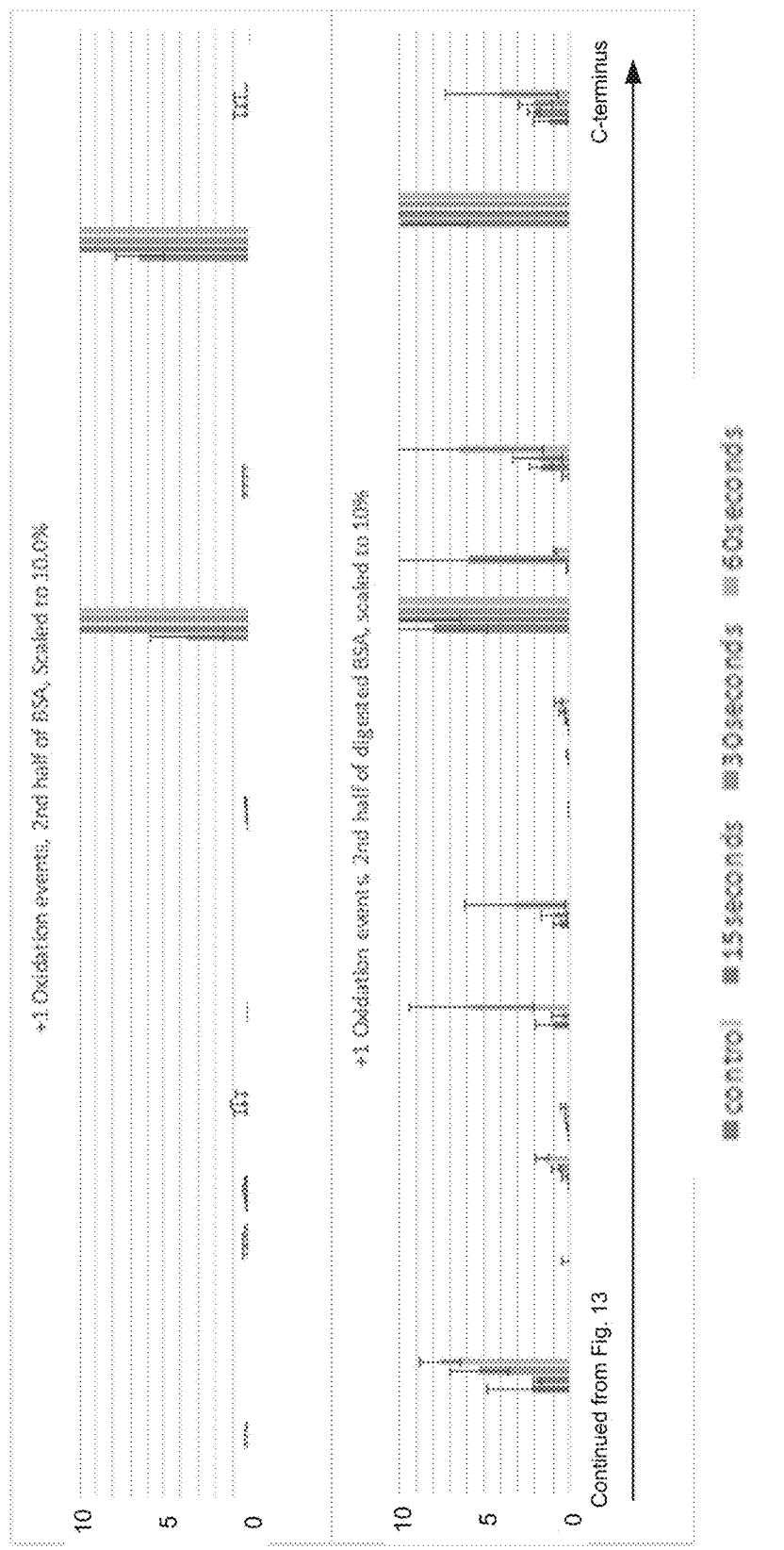
FIG. 14 is a pair of plots of oxidation of undigested and digested bovine serum albumin, as described in Example 6.
Figure 15:
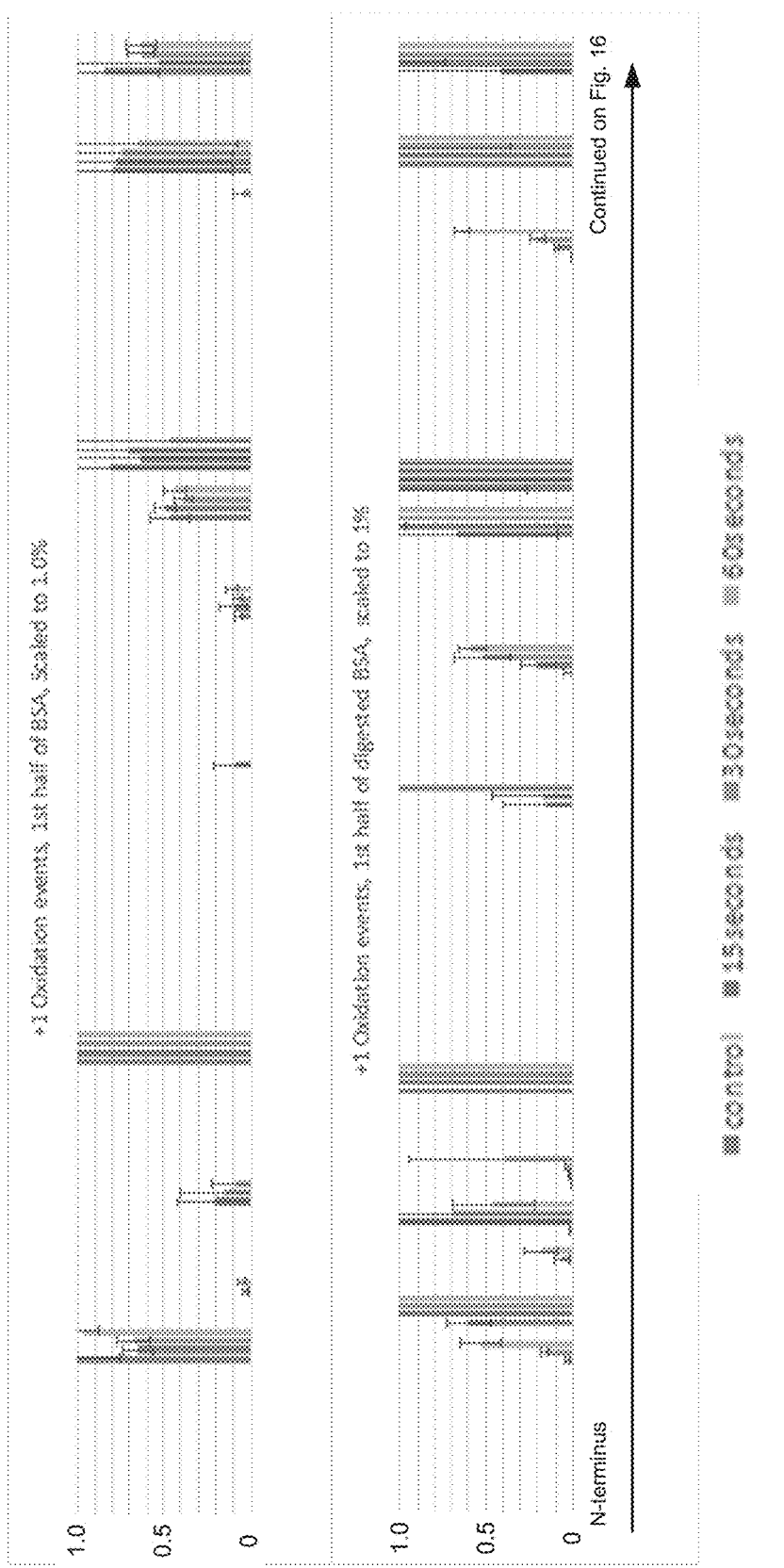
FIG. 15 is a pair of plots of oxidation of undigested and digested bovine serum albumin, as described in Example 6.
Figure 16:
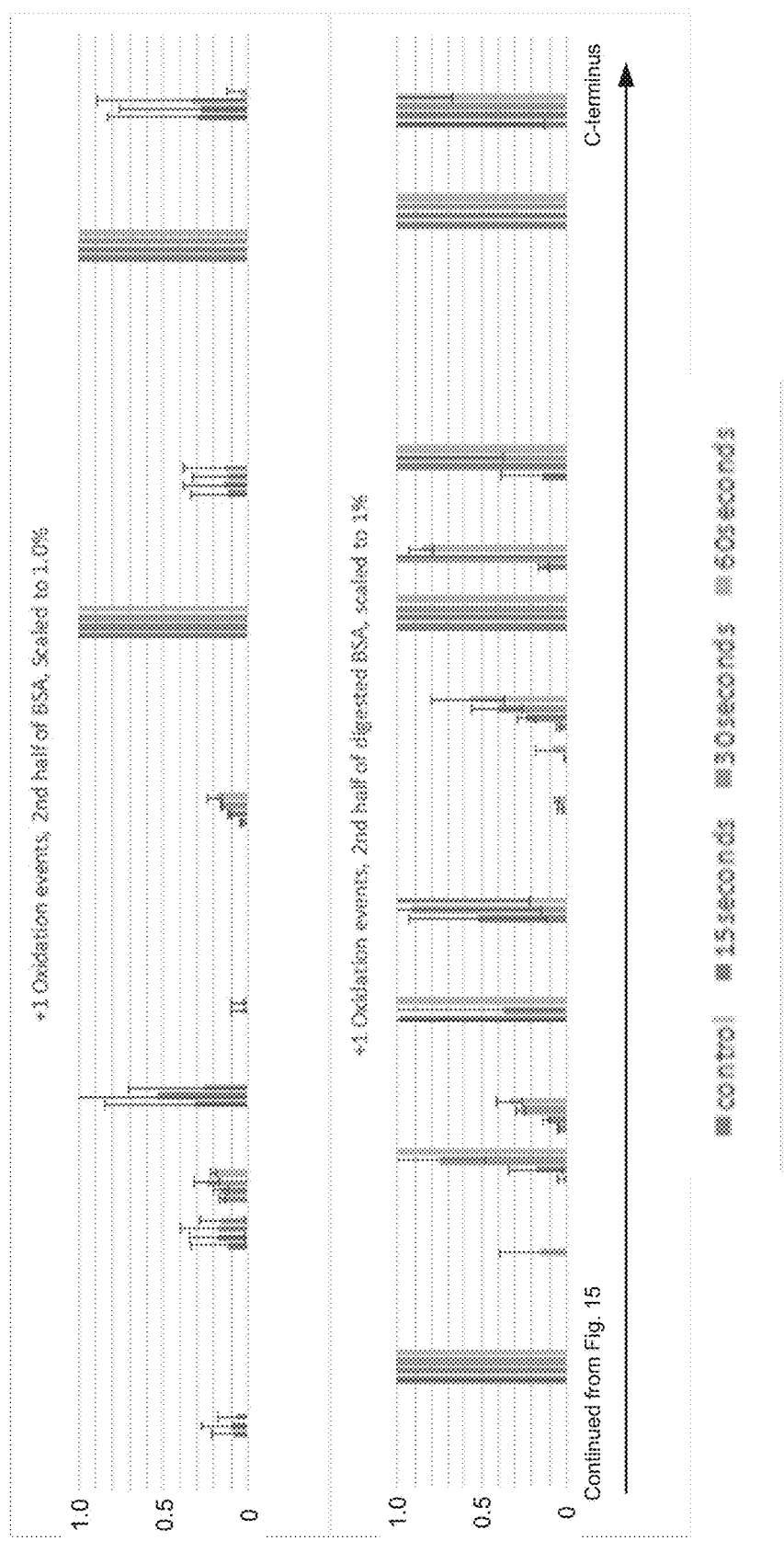
FIG. 16 is a pair of plots of oxidation of undigested and digested bovine serum albumin, as described in Example 6.

An undigest and digested bovine serum albumin sample in water were utilized as samples in an experimental setup similar to the one shown in FIG. 1 and the experimental parameters described in Example 1. Referring to FIGS. 11 to 16, plots comparing the oxidation levels for undigested (top) and digested (bottom) bovine serum albumin are shown. FIGS. 11 and 12 are scaled to 100%, FIGS. 13 and 14 are scaled to 10%, and FIGS. 15 and 16 are scaled to 1.0%. While the plots that are scaled to 100% appear somewhat similar, the plots scaled to 10% and 1.0% show major differences between the undigested experiment and the digested experiment. Specifically, these data show evidence that the oxidation of various residues is limited by reduced solvent interaction when the protein has not been digested. On the other hand, digestion makes most residues solvent accessible and the resulting oxidation levels in the digested experiment illustrates that more residues are accessible. This example confirms that the methods described herein are useful for studying solvent accessibility and a digested protein can be utilized as a benchmark for comparison with an undigested protein.

Example 7

Studying Solvent Accessibility for Protein Bound and Unbound by a Ligand

Figure 17:
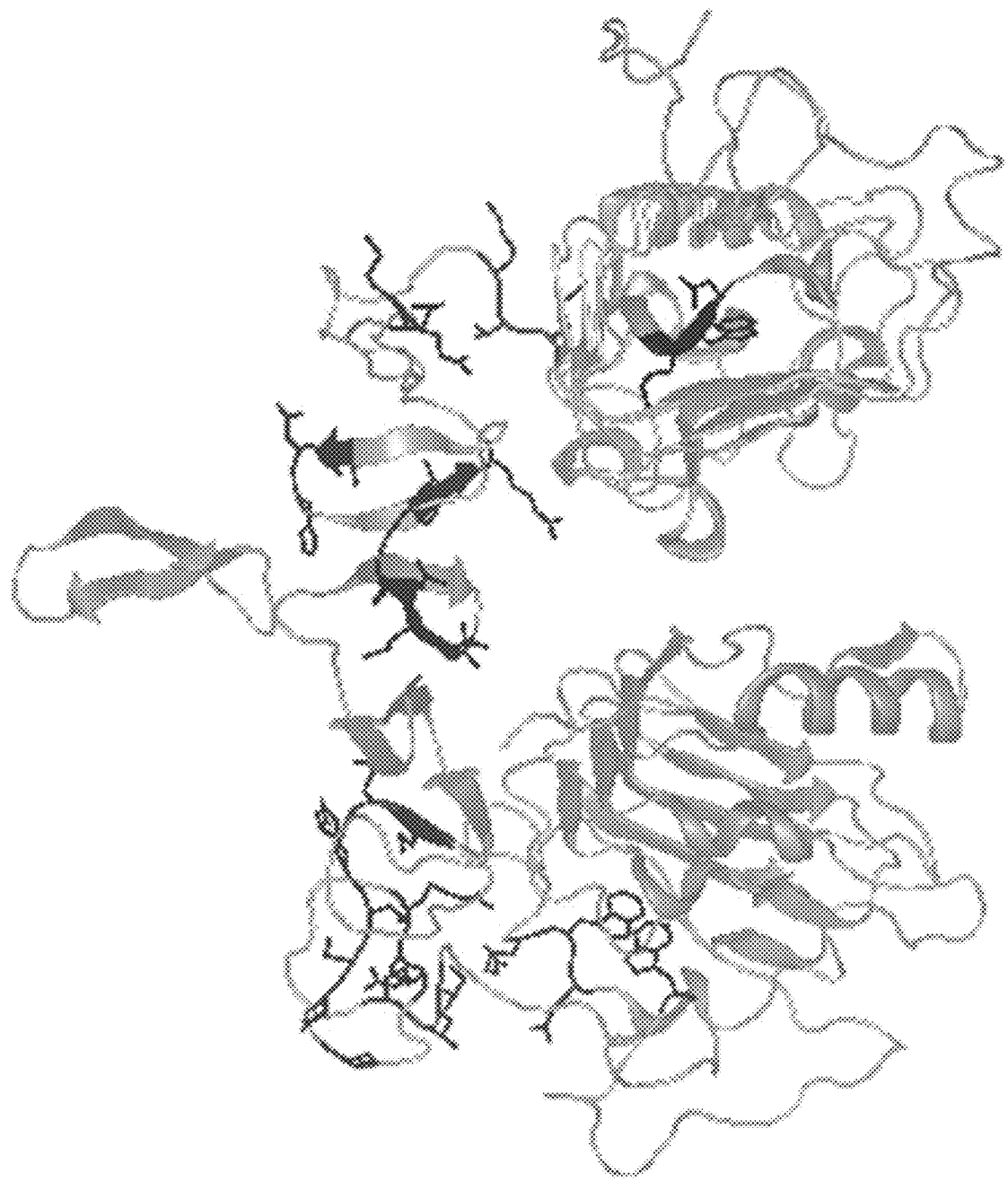
FIG. 17 is a crystal structure of epidermal growth factor receptor protein, showing residues with reduced oxidation when bound with epidermal growth factor.
Figure 18:
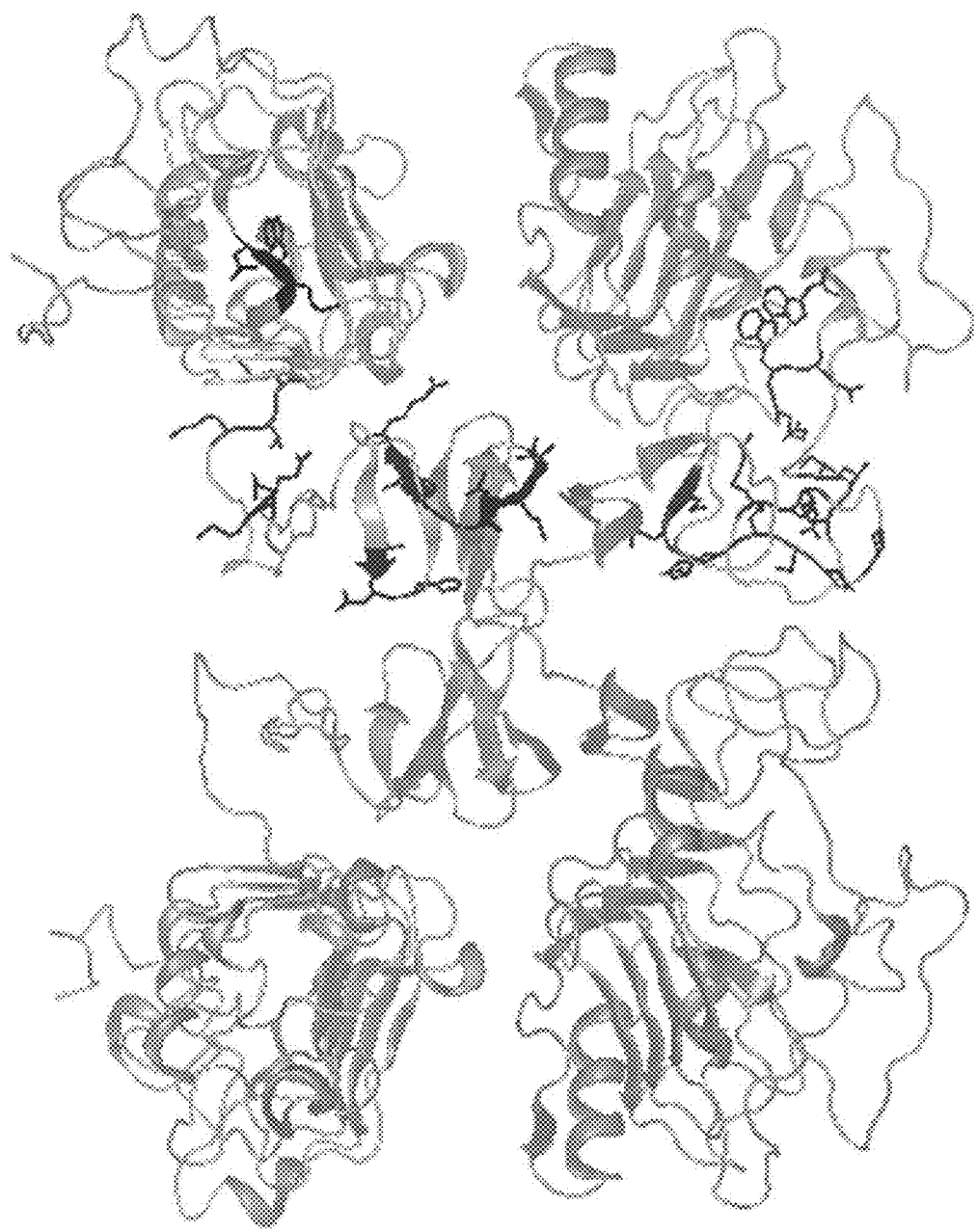
FIG. 18 is a crystal structure of epidermal growth factor receptor protein homodimer, showing residues with reduced oxidation when bound with epidermal growth factor.

An experimental setup similar to the one shown in FIG. 1 and the experimental parameters described in Example 1 were used in this Example. Referring to FIG. 17, the protein crystal structure of epidermal growth factor receptor (EGFR) protein is shown. Black residues represent residues where oxidation is greater in EGFR unbound to epidermal growth factor (EGF) when compared with oxidation of EGFR that is bound to EGF. Referring to FIG. 18, the protein crystal structure of an EGFR protein activated homodimer is shown. In both cases, EGF is not illustrated. It should be appreciated that many of the residues associated with the measured reduced oxidation (i.e., reduced oxidation when bound to EGF) are positioned at the interface of the EGFR homodimer, which implies that the areas of interaction in binding EGF and forming the activated homodimer (in addition to some residues that are remote from these areas of interaction) have reduced oxidation as a result of the structural modification of binding and dimerization.

Although the invention has been described in considerable detail with reference to certain aspects, one skilled in the art will appreciate that the present invention can be practiced by other than the described embodiments, which have been presented for purposes of illustration and not of limitation. Therefore, the scope of the appended claims should not be limited to the description of the embodiments contained herein.

We claim:

1. A method of modifying a biological molecule located in a sample, the sample contacted by a fluid or enclosed within a confined space, the sample or the fluid containing a plurality of marker radical precursors, the method comprising the following steps:
    a) generating a sequence of plasma pulses in the fluid and/or generating the sequence of plasma pulses within the sample, the sequence of plasma pulses in the fluid having at least a portion of the sequence of plasma pulses within 1 cm of the sample, thereby converting one or more of the plurality of marker radical precursors into one or more marker radicals, wherein the plasma pulses have a pulse width of between 1 ps and 1 ms, the sequence of plasma pulses have a pulse repetition rate of between 1 Hz and 100 GHz, or the sequence of plasma pulses are generated for a total length of time of between 1 ns and 1 hour, wherein the plasma of step a) is generated by a voltage in a range of between 1V and 1 MV; and
    b) waiting a length of time sufficient for the one or more marker radicals to interact with the biological molecule, thereby modifying the biological molecule,
    wherein steps a) and b) cause a detectable difference in the biological molecule without initiating denaturation of the biological molecule.

2. The method of claim 1, wherein the plasma pulses have a pulse width of between 1 ps and 1 ms and the sequence of plasma pulses have a pulse repetition rate of between 1 Hz and 100 GHz.

3. The method of claim 2, wherein the plasma pulses have a pulse width of between 1 ps and 1 ms, the sequence of plasma pulses have a pulse repetition rate of between 1 Hz and 100 GHz, and the sequence of plasma pulses are generated for a total length of time of between 1 ns and 1 hour.

4. The method of claim 1, wherein the plasma of step a) is generated by a plasma jet.

5. The method of claim 1, wherein the plasma of step a) is generated by a voltage in a range of between 500 V and 100 kV.

6. The method of claim 1, wherein the generating of step a) is configured to provide a peak concentration of marker radicals in the sample in a range of between 50 nM and 800 µM.

7. The method of claim 1, wherein the generating of step a) elevates a temperature of the sample by an amount less than 50° C.

8. The method of claim 1, wherein the generating of step a) transfers an amount of energy to the sample of less than 360 MJ.

9. The method of claim 1, wherein the sample has a volume of between 1 µL and 400 L.

10. The method of claim 1, wherein the fluid is a gas containing the plurality of marker radical precursors.

11. The method of claim 1, wherein the plurality of marker radical precursors is a plurality of water molecules.

12. The method of claim 1, wherein the sample is selected from the group consisting of blood, blood plasma, urine, saliva, lymph, tears, sweat, cerebrospinal fluid, amniotic fluid, aqueous humour, vitreous humour, bile, breast milk, cerumen, chyle, chime, endolymph, perilymph, exudates, feces, female ejaculate, gastric acid, gastric juice, mucus, pericardial fluid, peritoneal fluid, pleural fluid, pus, rheum, sebum, serous fluid, semen, smegma, sputum, synovial fluid, vaginal secretion, vomit, living bacterial cultures, living tissue or eukaryotic cell cultures, and combinations thereof.

13. The method of claim 1, wherein the sample is selected from the group consisting of eukaryotic intracellular fluid, eukaryotic extracellular fluid, prokaryotic intracellular fluid, prokaryotic extracellular fluid, homogenized tissue, homogenized cells, homogenized tissue culture, homogenized cell culture, homogenized plant tissue, and combinations thereof.

14. The method of claim 1, wherein the sample comprises the biological molecule and a buffer solution.

15. The method of claim 1, wherein the buffer solution comprises phosphate buffered saline, tris(hydroxymethyl)aminomethane, tris hydrochloric acid, ammonium bicarbonate, 4-(2-hydroxyethyl)-1-piperazineethanesulfonic acid, 3 (N morpholino)propanesulfonic acid, 2-(N-morpholino)ethanesulfonic acid, 2,2-Bis(hydroxymethyl)-2,2',2"-nitrilotriethanol (bis-tris), N-(2-Acetamido)iminodiacetic acid, piperazine-N,N'-bis(2-ethanesulfonic acid) (PIPES), N-(2-Acetamido)-2-aminoethanesulfonic acid (ACES), 3-(N-morpholinyl)-2-hydroxypropanesulfonic acid sodium salt, 1,3-bis(tris(hydroxymethyl)methylamino)propane, N,N-Bis(2-hydroxyethyl)-2-aminoethanesulfonic acid, 2-[[1,3-dihydroxy-2-(hydroxymethyl)propan-2-yl]amino]ethanesulfonic acid, 3-(Bis(2-hydroxyethyl)amino)-2-hydroxypropane-1-sulfonic acid, 3-[[1,3-dihydroxy-2-(hydroxymethyl)propan-2-yl]amino]-2-hydroxypropane-1-sulfonic acid, 2 amino-2-(hydroxymethyl)-1,3-propanediol, piperazine-1,4-bis(2-hydroxypropanesulfonic acid) dihydrate, 3-[4-(2-Hydroxy-1,1-bis(hydroxymethyl)ethyl)glycine, glycylglycine, 2-(Bis(2-hydroxyethyl)amino)acetic acid, N-(2-hydroxyethyl)piperazine-N'-(4-butanesulfonic acid), 3-[[1,3-dihydroxy-2-(hydroxymethyl)propan-2-yl]amino]propane-1-sulfonic acid, 2-amino-2-methyl-1,3-propanediol, N-(1,1-Dimethyl-2-hydroxyethyl)-3-amino-2-hydroxypropanesulfonic acid, N-cyclohexyl-2-aminoethanesulfonic acid, N-cyclohexyl-2-hydroxyl-3-aminopropanesulfonic acid, 1-amino-2-methyl-1-propanol, N-cyclohexyl-3-aminopropanesulfonic acid, 4-(cyclohexylamino)-1-butanesulfonic acid, Lysogeny broth, or a combination thereof.

16. The method of claim 1, wherein the biological molecule is selected from the group consisting of a nucleic acid molecule, a protein, a lipid, a biological metabolite, and combinations thereof.

17. A method of determining if a portion of a biological molecule is accessible to a solvent, the biological molecule and the solvent contained in a sample, the sample contacted by a fluid or enclosed within a confined space, the sample or the fluid containing a marker radical precursor, the method comprising the following steps:
   a) oxidizing, by way of a plasma that introduces marker radicals to the sample, the biological molecule, wherein the oxidizing occurs in the presence of oxygen, wherein the oxidizing occurs while the biological molecule is in solution within the solvent, and wherein the plasma is configured to elevate a temperature of the sample by an amount less than would begin denaturation of the biological molecule;
   b) subsequent to step a), assessing whether the portion of the biological molecule was oxidized by the oxidizing of step a), wherein the presence of oxidizing indicates that the portion is accessible to the solvent and the absence of oxidizing indicates that the portion is inaccessible to the solvent; and
   c) generating a report indicating whether the portion is accessible to the solvent or inaccessible to the solvent.

18. The method of claim 17, wherein the assessing of step b) comprises performing a mass spectrometry analysis of the biological molecule.

19. A method of assessing a biological sample containing one or more biological molecules having one or more solvent accessible portions and one or more solvent inaccessible portions, the method comprising the following steps:
   a) acquiring a first subsample and a second subsample of the biological sample, the first sub sample and the second subsample containing substantially equivalent concentrations of the one or more biological molecules;
   b) introducing a denaturing factor into the second subsample of the biological sample, the denaturing factor configured to alter at least a portion of the one or more biological molecules located within the second subsample to expose at least a portion of the solvent inaccessible portions to solvent;
   c) oxidizing, by way of a plasma that introduces marker radicals to the first subsample and the second subsample, the one or more biological molecules in the first subsample and the second subsample, wherein the plasma is configured to elevate a temperature of the first sub sample and the second subsample by an amount less than would begin denaturation of the one or more biological molecules;
   d) subsequent to step c), assessing a difference in oxidization levels between the one or more biological molecules in the first subsample and the second subsample, thereby identifying at least a portion of the one or more solvent inaccessible portions; and e) generating a report indicating the identification of the at least a portion of the one or more solvent inaccessible portions.

20. The method of claim 19, wherein the assessing of step b) comprises performing a mass spectrometry analysis of the biological molecule.

* * * * *

UNITED STATES PATENT AND TRADEMARK OFFICE
CERTIFICATE OF CORRECTION

PATENT NO. : 10,571,460 B2
APPLICATION NO. : 15/600352
DATED : February 25, 2020
INVENTOR(S) : Michael R Sussman et al.

Page 1 of 1

It is certified that error appears in the above-identified patent and that said Letters Patent is hereby corrected as shown below:

In the Specification

Column 5, Line 60, "(.OH)" should be --($\cdot$OH)--.

Column 5, Line 61, "(H.)" should be --(H$\cdot$)--.

Column 5, Line 61, "(.NO$_2$)" should be --($\cdot$NO$_2$)--.

Column 5, Line 62, "(.NO$_3$)" should be --($\cdot$NO$_3$)--.

Column 5, Line 62, "(.OOH)" should be --($\cdot$OOH)--.

Column 9, Line 9, "(AN/IPSO)" should be --(AMPSO)--.

Signed and Sealed this
Fifth Day of May, 2020

Andrei Iancu
*Director of the United States Patent and Trademark Office*